US011298407B2

(12) United States Patent
Kluger et al.

(10) Patent No.: US 11,298,407 B2
(45) Date of Patent: Apr. 12, 2022

(54) HEMOGLOBIN BASED OXYGEN CARRIER AND METHOD OF PREPARATION

(71) Applicant: THE GOVERNING COUNCIL OF THE UNIVERSITY OF TORONTO, Toronto (CA)

(72) Inventors: Ronald Henry Kluger, Toronto (CA); Serena Singh, Toronto (CA); Ina Dubinsky-Davidchik, Toronto (CA)

(73) Assignee: THE GOVERNING COUNCIL OF THE UNIVERSITY OF TORONTO, Toronto (CA)

(*) Notice: Subject to any disclaimer, the term of this patent is extended or adjusted under 35 U.S.C. 154(b) by 142 days.

(21) Appl. No.: 16/335,328

(22) PCT Filed: Sep. 21, 2017

(86) PCT No.: PCT/CA2017/051111
§ 371 (c)(1),
(2) Date: Mar. 21, 2019

(87) PCT Pub. No.: WO2018/053634
PCT Pub. Date: Mar. 29, 2018

(65) Prior Publication Data
US 2020/0016242 A1 Jan. 16, 2020

Related U.S. Application Data

(60) Provisional application No. 62/418,907, filed on Nov. 8, 2016, provisional application No. 62/397,546, filed on Sep. 21, 2016.

(51) Int. Cl.
| | |
|---|---|
| *A61K 35/14* | (2015.01) |
| *A61K 38/42* | (2006.01) |
| *A61K 47/64* | (2017.01) |
| *A61K 47/55* | (2017.01) |

(52) U.S. Cl.
CPC .............. *A61K 38/42* (2013.01); *A61K 47/55* (2017.08); *A61K 47/643* (2017.08); *A61K 47/6445* (2017.08)

(58) Field of Classification Search
None
See application file for complete search history.

(56) References Cited

U.S. PATENT DOCUMENTS 5,917,020 A * 6/1999 Kluger .................. C07C 233/81
530/385
8,703,936 B2 4/2014 Jewett et al.

FOREIGN PATENT DOCUMENTS

WO WO-03087768 A2 * 10/2003 ......... G01N 33/5079
WO WO-2013003555 A1 * 1/2013 ............. C07K 1/107

OTHER PUBLICATIONS

Foot, J. S., Chemical Communications, (2009) 7315-7317 (Year: 2009).*
Baskin, J. M., Proc. Natl. Acad. Sci. U. S. A., (2007), 104, 16793-16797 (Year: 2007).*
Webster, Layola University Dissertation, May 2016 (Year: 2016).*
STNext search notes-SEQ-ID-2, WO 03087768, 1 page, 2021 (Year: 2021).*
Webster. K. D. (May 2016) Development of "Inside-Out" PEGylated Crosslinked Hemoglobin Polymers: Novel Hemoglobin-Based Oxygen Carriers (HBOC) Dissertations, Paper 1976, as retrieved from the internet at http://ecommons.luc.edu/luc diss/1976.
Webster. K. D. et al., (Apr. 2016) Development of "Inside-Out" PEGylated crosslinked hemoglobin Polymers: A Novel Hemoglobin-Based Oxygen Carriers (HBOC) FASEB J 30, Suppl. 825.3.
Singh, S. et al (Sep. 14, 2015) Subunit-directed click coupling via double crosslinked hemoglobin efficiently produces readily purified functional bis-tetrameric oxygen carriers. Org Biomol Chem 13: 11118-11128.
Singh, S. et al. (Sep. 27, 2016) Strain-promoted azide-alkyne cycloaddition for protein-protein coupling in the formation of a bis-hemoglobin as a copper-free oxygen carrier. Org Biomol Chem 14: 10011-10017.
International Search Report and Written Opinion of PCT/CA2017/051111.
Agard, N. J., J. A Prescher and C. R. Bertozzi, A Strain-Promoted [3+2] Azide-Alkyne Cycloaddition for Covalent Modification of Biomolecules in Living Systems J. Am. Chem. Soc., 2004, 126, 15046-15047.

(Continued)

*Primary Examiner* — Satyanarayana R Gudibande
(74) *Attorney, Agent, or Firm* — Norton Rose Fulbright Canada LLP

(57) ABSTRACT

The disclosure concerns a class of hemoglobin based oxygen carriers (HBOCs) comprising a first hemoglobin protein cross-linked by a chemical reaction that is followed by a strain-promoted alkyne-azide cycloaddition (SPAAC) reaction or by a strain-promoted alkyne-nitrone cycloaddition (SPANC) in the absence of added copper salts to a second modified cross-linked hemoglobin protein. The resulting construct is an HBOC that is capable of binding oxygen and releasing same in a useful manner upon addition in an appropriate solution to the circulatory system of a patient. The disclosure also concerns a method of production of the HBOC where a first and second hemoglobin protein are produced by covalently linking hemoglobin to an angle strained cycloalkyne moiety. A compound comprising at least 2 azide or nitrone moieties is then added for reacting under conditions conducive to SPAAC or SPANC in reaction in absence of copper ions with the first and second hemoglobin protein for causing covalent linkage of the first and second hemoglobin protein to the compound comprising said at least 2 azide or nitrone moieties, resulting in said HBOC. The HBOC can be used for transfusion, perfusion or for increasing oxygen transport.

18 Claims, 10 Drawing Sheets

Specification includes a Sequence Listing.

(56) References Cited

OTHER PUBLICATIONS

Baskin, J. M., J. A Prescher, S. T. Laughlin, N. J. Agard, P. V. Chang, I. A Miller, A Lo, J. A Codelli and C. R. Bertozzi, Copper-free click chemistry for dynamic in vivo imaging Proc. Natl. Acad. Sci. U. S. A, (2007), 104, 16793-16797.
Hu, D. and Kluger, R., Biochemistry, Functional Cross-Linked Hemoglobin Bis-tetramers: Geometry and Cooperativity (2008) 47, 12551-12561.
Foot, J. S., Lui, F. E., and Kluger, R., Hemoglobin bis-tetramers via cooperative azide-alkyne coupling, Chemical Communications, (2009) 7315-7317.
Haruki, R., Kimura, T., Iwasaki, H., Yamada, K., Kamiyama, I., Kohno, M., Taguchi, K., Nagao, S., Maruyama, T., Otagiri, M., and Komatsu, T. Safety Evaluation of Hemoglobin-Albumin Cluster "HemoAct" as a Red Blood Cell Substitute, Scientific Reports 5, 12778.
Lui, F. E., Yu, B., Baron, D. M., Lei, C., Zapel, W. M., and Kluger, R. (2012) Hemodynamic responses to a hemoglobin bis-tetramer and its polyethylene glycol conjugate (2015), Transfusion 52, 974-982.
Vandegriff, K. D., Young, M. A., Keipert, P. E., and Winslow, R. M.) The safety profile of Hemospan®: a new oxygen therapeutic designed using maleimide poly(ethylene) glycol conjugation to human hemoglobin, Transfusion Alternatives in Transfusion Medicine (2007) 9, 213-225.
Abel, G. R., Z. A. Calabrese, J. Ayco, J. E. Hein and T. Ye, Bioconjugate Chem., 2016, 27, 698-704.
Alagic, A., A. Koprianiuk and R. Kluger, J. Am. Chem. Soc., 2005, 127, 8036-8043.
Arndt, C., S. Koristka, H. Bartsch and M. Bachmann, in Protein Electrophoresis, ed. B. T. Kurien and R. H. Scofield, Humana Press, 2012, vol. 869, ch. 5, pp. 49-53.
Buehler, P. W., D'Agnillo, F., and Schaer, D. J. Hemoglobin-based oxygen carriers: from mechanisms of toxicity and clearance to rational drug design, Trends in Molecular Medicine 16, 447-457.
Caccia, D., Ronda, L., Frassi, R., Perrella, M., Del Favero, E., Bruno, S., Pioselli, B., Abbruzzetti, S., Viappiani, C., and Mozzarelli, A. (2009) PEGylation Promotes Hemoglobin Tetramer Dissociation, Bioconjugate Chemistry 20, 1356-1366.
Chang, P. V., J. A. Prescher, E. M. Sletten, J. M. Baskin, I. A. Miller, N. J. Agard, A. Lo and C. R. Bertozzi, Proc. Natl. Acad. Sci. U. S. A., 2010, 107, 1821-1826.
Chen, J.-Y. et al., ., Scerbo, M., and Kramer, G. (2009) A Review of Blood Substitutes: Examining The History, Clinical Trial Results, and Ethics of Hemoglobin-Based Oxygen Carriers, Clinics (Sao Paulo, Brazil) 64, 803-813.
Deroo, S., Stengel, F., Mohammadi, A., Henry, N., Hubin, E., Krammer, E. M., Aebersold, R. and Raussens, V., ACS Chem. Biol., 2015, 10, 1010-1016.
Desfougères, Y., Croguennec, T., Lechevalier, V., Bouhallab, S., and Nau, F. (2010) Charge and Size Drive Spontaneous Self-Assembly of Oppositely Charged Globular Proteins into Microspheres, The Journal of Physical Chemistry B 114, 4138-4144.
Gaetke, L. M. and C. K. Chow, Toxicology, 2003, 189, 147-163.
Green, N. M. (1970) Spectrophotometric determination of avidin and biotin, In Methods in Enzymology, pp. 418-424, Academic Press.
Gruttner, C., K. Muller and J. Teller, IEEE Trans. Magn., 2013, 49, 172-176.
Guarnone, R., Centenara, E., and Barosi, G. (1995) Performance characteristics of Hemox-Analyzer for assessment of the hemoglobin dissociation curve, Haematologica 80, 426-430.
Guillochon, D., Vijayalakshmi, M. W., Thiam-Sow, A., Thomas, D., and Chevalier, A. (1986) Effect of glutaraldehyde on hemoglobin: functional aspects and Mössbauer parameters, Biochemistry and Cell Biology 64, 29-37.

Harris, D. R., and Palmer, A. F. (2008) Modern Cross-linking Strategies for Synthesizing Acellular Hemoglobin-Based Oxygen Carriers, Biotechnology progress 24, 1215-1225.
Hong, V., S. I. Presolski, C. Ma and M. G. Finn, Angew. Chem., Int. Ed., 2009, 48, 9879-9883.
Jonathan, S. J., Arezou Sadighi, A., and Randall, J. H. (2012) Crosslinked, Polymerized, and PEG-Conjugated Hemoglobin-Based Oxygen Carriers: Clinical Safety and Efficacy of Recent and Current Products, Current Drug Discovery Technologies 9, 158-165.
Kim-Shapiro, D. B., A. N. Schechter and M. T. Gladwin, Arterioscler., Thromb., Vasc. Biol., 2006, 26, 697-705.
Kluger, R. and Y. Song, J. Org. Chem., 1994, 59, 733-736.
Kluger, R. and Alagic, A., Bioorg. Chem., 2004, 32, 451-472.
Kluger, R., J. S. Foot and A. A. Vandersteen, Chem. Commun., 2010, 46, 1194-1202.
Kluger, R., Song, Y., Wodzinska, J., Head, C., Fujita, T. S., and Jones, R. T. (1992) Trimesoyltris(3,5-dibromosalicylate): specificity of reactions of a trifunctional acylating agent with hemoglobin, Journal of the American Chemical Society 114, 9275-9279.
Kluger, R., Wodzinska, J., Jones, R. T., Head, C., Fujita, T. S., and Snih, D. T. (1992) Three-point crosslinking: potential red cell substitutes from the reaction of trimesoyl tris(methyl phosphate) with hemoglobin, Biochemistry 31, 7551-7559.
Kolb, H. C., M. G. Finn and K. B. Sharpless, Angew. Chem., Int. Ed., 2001, 40, 2004-2021.
Liljeström, V., Mikkilä, J., and Kostiainen, M. A. (2014) Self-assembly and modular functionalization of three-dimensional crystals from oppositely charged proteins, Nat Commun 5.
Livnah, O., Bayer, E. A., Wilchek, M., and Sussman, J. L. (1993) Three-dimensional structures of avidin and the avidin-biotin complex, Proceedings of the National Academy of Sciences of the United States of America 90, 5076-5080.
Lui, F. E. and Kluger, R., Biochemistry, 2009, 48, 11912-11919.
Lui, F. E., Dong, P., and Kluger, R. (2008) Polyethylene Glycol Conjugation Enhances ite Reductase Activity of Native and Cross-Linked Hemoglobin, Biochemistry 47, 10780.
Mozzarelli, A., Ronda, L., Faggiano, S., Bettati, S., and Bruno, S. (2010) Haemoglobin-based oxygen carriers: research and reality towards an alternative to blood transfusions, Blood Transfusion 8, s59-s68.
Ning et al., Angew. Chem. Ed. 2010, 49, 3065-3068.
Ornelas, C., J. Broichhagen and M. Weck, J. Am. Chem. Soc., 2010, 132, 3923-3931.
Petronzelli, F., Pelliccia, A., Anastasi, A. M., Lindstedt, R., Manganello, S., Ferrari, L. E., Albertoni, C., Leoni, B., Rosi, A., D'Alessio, V., Deiana, K., Paganelli, G., and De Santis, R. (2010) Therapeutic Use of Avidin is Not Hampered by Antiavidin Antibodies in Humans, Cancer Biotherapy and Radiopharmaceuticals 25, 563-570.
Popik V. Org. Biomol. Chem., Oct. 3, 2012, 10(41) 8200-8202.
Ramil and Lin Chem Commun 2013 49 11007-11022.
Repo, S., Paldanius, T. A., Hytönen, Vesa P., Nyholm, T. K. M., Halling, Katrin K., Huuskonen, J., Pentikäinen, Olli T., Rissanen, K., Slotte, J. P., Airenne, T. T., Salminen, T. A., Kulomaa, Markku S., and Johnson, Mark S. (2006) Binding Properties of HABA-Type Azo Derivatives to Avidin and Avidin-Related Protein 4, Chemistry & Biology 13, 1029-1039.
Rifkind, J. M., L. D. Lauer, S. C. Chiang and N. C. Li, Biochemistry, 1976, 15, 5337-5343.
Schiffner, T., N. de Val, R. A. Russell, S. W. De Taeye, A. T. De la Pena, G. Ozorowski, H. J. Kim, T. Nieusma, F. Brod, A. Cupo, R. W. Sanders, J. P. Moore, A. B. Ward and Q. J. Sattentau, J. Virol., 2016, 90, 813-828.
Schoffelen, S., J. Beekwilder, M. F. Debets, D. Bosch and J. C. M. V. Hest, Bioconjugate Chem., 2013, 24, 987-996.
Schumacher, M. A., Dixon, M. M., Kluger, R., Jones, R. T. and Brennan, R. G., Nature, 1995, 375, 84-87.
Sinz, A., C. Arlt, D. Chorev and M. Sharon, Protein Sci., 2015, 24, 1193-1209.
Siren, E. M. J., S. Singh and R. Kluger, Org. Biomol. Chem., 2015, 13, 10244-10249.
Snyder, S. R., Welty, E. V., Walder, R. Y., Williams, L. A., and Walder, J. A. (1987) HbXL99 alpha: a hemoglobin derivative that

(56) References Cited

OTHER PUBLICATIONS is cross-linked between the alpha subunits is useful as a blood substitute, Proceedings of the National Academy of Sciences 84, 7280-7284.

Wang, Z.-X., Ravi Kumar, N., and Srivastava, D. K. (1992) A novel spectroscopic titration method for determining the dissociation constant and stoichiometry of protein-ligand complex, Analytical Biochemistry 206, 376-381.

Wendeln, C., I. Singh, S. Rinnen, C. Schulz, H. F. Arlinghaus, G. A. Burley and B. J. Ravoo, Chem. Sci., 2012, 3, 2479-2484.

Yang, H., P. Srivastava, C. Zhang and J. C. Lewis, ChemBioChem, 2014, 15, 223-227.

Yang, Y. and R. Kluger Chem. Commun., 2010, 46, 7557-7559.

Yu, S., Yao, P., Jiang, M., and Zhang, G. (2006) Nanogels prepared by self-assembly of oppositely charged globular proteins, Biopolymers 83, 148-158.

Zeng, D., B. M. Zeglis, J. S. Lewis and C. J. Anderson, J. Nucl. Med., 2013, 54, 829-832.

\* cited by examiner

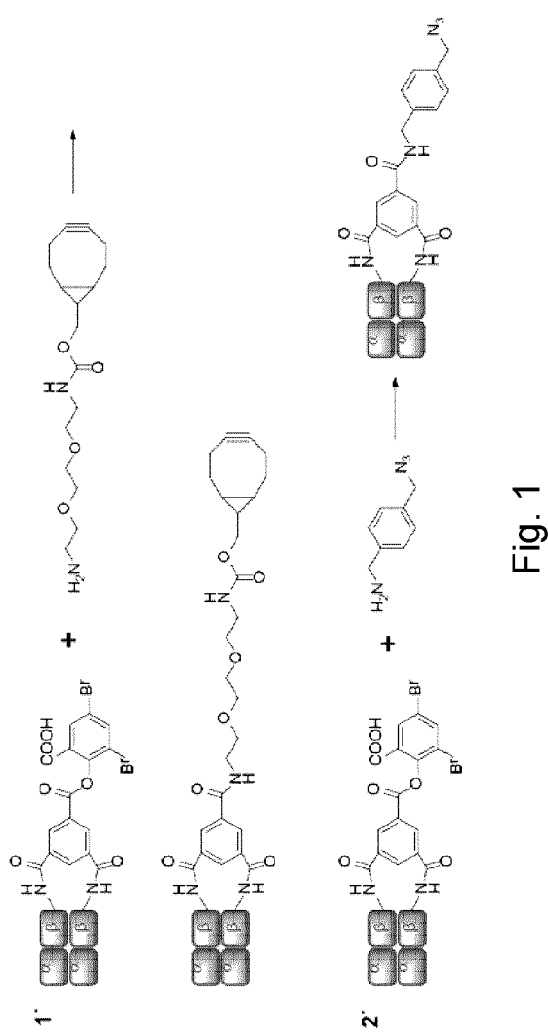
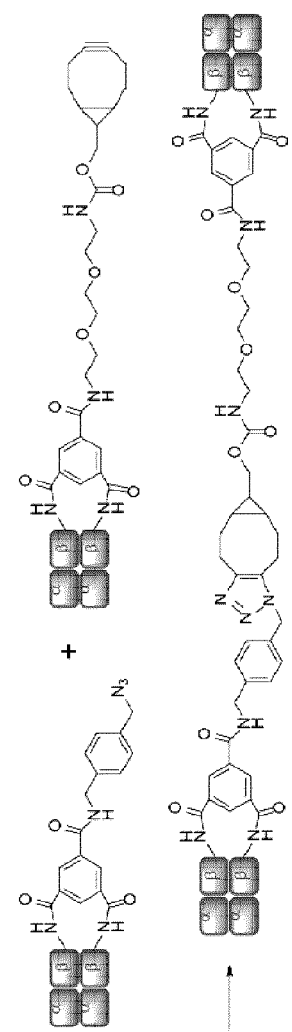
Fig. 1
Fig. 2 n = 1 to 6
linkers per Hb subunit m = 1 to 3
albumins per Hb dimer

HEMOGLOBIN BASED OXYGEN CARRIER AND METHOD OF PREPARATION

CROSS-REFERENCE TO RELATED APPLICATIONS AND DOCUMENTS

This application claims priority from U.S. provisional patent applications 62/397,546 filed on Sep. 21, 2016 and 62/418,907 filed on Nov. 8, 2016. A sequence listing in electronic form is being filed concurrently. The content of the priority applications and of the sequence listing are herewith incorporated herein by reference in their entirety.

TECHNOLOGICAL FIELD

The present disclosure relates to a hemoglobin-based oxygen carrier (HBOC), in particular to hemoglobin bis-tetramers, and to a method for preparing the protein assemblies by the strain-promoted alkyne-azide cycloaddition. The invention also pertains to the use of the hemoglobin bis-tetramers in a method for increasing oxygen transport in vivo in an individual or for use in transfusions or perfusions.

BACKGROUND

The potential use of modified hemoglobin as a substitute for red blood cells in transfusions or perfusions is widely documented to fill a critical need in medical therapeutics. Circulating red blood cells serve to deliver oxygen to tissues. A significant decrease of red blood cells in circulation, typically from loss of blood in trauma or from disease, can result in serious and irreversible damage to organs due to the lack of available oxygen. While administration of plasma or saline can replace lost volume, oxygenation capacity must also be restored to reduce potential morbidity. Red blood cells present problems with respect to administration (typing), storage, timely availability, and are a source of potential infection. Thus, a product that would replace red blood cells to deliver oxygen to tissues in certain circumstances, or to maintain through perfusion an organ awaiting to be transplanted continues to be widely sought.

Hemoglobin is the oxygen-carrying component of the red cell. Unmodified hemoglobin is a tetrameric assembly of protein components consisting of two sets of paired subunits, each with a heme prosthetic group to which oxygen binds. Human adult hemoglobin is tetrameric having a molecular weight of approximately 64 kD. It is structurally comprised of two alpha and two beta subunits with the alpha/beta subunits forming pairs called dimers. Acellular hemoglobin cannot be used as a replacement for lost cellular material as it dissociates into its dimeric subunits. The dissociated form is not a useful oxygen carrier and also is the source of serious side effects. Thus, a chemical cross-link or its equivalent that prevents separation of the subunits is necessary for hemoglobin to be used in an acellular state. In that case it is expected that hemoglobin will deliver oxygen to cells if it is first oxygenated and if its affinity for oxygen is lower than that of the target cell. In addition, stabilized derivatives of hemoglobin have been previously tested clinically and it was found that in some cases the materials induced symptoms that are most likely related to induced hypertension. In those cases, the added hemoglobin derivatives appear to cause vasoconstriction that is likely to be a result of their scavenging of endothelial nitric oxide. This can occur if the modified tetramer extravasates through the endothelia where they scavenge endogenous nitric oxide, the signal required for relaxation of the muscles surrounding the blood vessel.

Hemoglobin (Hb)-based oxygen carriers (HBOCs) are also known as a component of a "blood substitute". Various potential HBOCs have been investigated over the last two decades with varying degrees of success.

For use in humans, blood-substitutes must contain no unstabilized hemoglobin. Early attempts to polymerize native hemoglobin by chemical reagents provided undefined mixtures that contained materials that remained vasoactive. Therefore, an HBOC suitable for human use requires a highly purified material that does not cause any side effects, vasoactivity being a central issue that was not widely recognized until clinical trials had been conducted.

For example, hemoglobin treated with a polymerizing agent was typically passed through a 100 kD filter to remove lower molecular weight hemoglobin derivatives from hemoglobin polymers. However, those processes have not been capable of producing material that is free of species similar in size to the core tetramers and dimers.

It was anticipated that protein assemblies that are about twice the size of the hemoglobin tetramer would avoid extravasation and scavenging of nitric oxide. Thus, it was shown that an assembly consisting of two tetramers did not raise blood pressure in sensitive animals where even a small amount of a single tetramer produces a very significant blood pressure increase. In addition, measurements of the effects of the coupled hemoglobins, "bis-tetramers" were shown to be effective oxygen carriers that did not induce hypertension in the same animals. However, reports of production of an effective oxygen-carrying bis-tetramer derived from hemoglobin in a pure state note that the processes are inefficient and the final product requires extensive purification to avoid contamination by smaller assemblies that would be subject to extravasation, potentially inducing clinical complications.

In the past, the inventors and others have tried to produce hemoglobin bis-tetramers with some level of success. For example, Dr. Kluger, one of the present inventors, along with his coworkers, reported in 2009 (Foot et al.) hemoglobin bis-tetramer formation via cooperative azide-alkyne coupling which required copper ions as a catalyst (CuAAC), which, free in circulation can cause toxicity.

To date, it is known that the administration of some potential HBOCs administered to normal and diseased animals results in (1) tissue oxygenation, (2) transient blood pressure elevation and (3) potential for heme loss and toxicity. Therefore, a need exists to improve the efficiency of the hemoglobin assembly and to improve the yield of the desired hemoglobin derivatives, while avoiding contamination with smaller entities.

Chemical cross-linking of individual proteins is a highly developed area with many applications and examples. Extending the approach that creates linkages within proteins to protein-protein coupling can produce novel entities with designed properties. Constructs of two hemoglobin (Hb) proteins coupled together, known as Hb bis-tetramers, have been found useful as circulating oxygen carriers that avoid extravasation from the vasculature (Lui, et al., Transfusion, 2012, 52, 974-982). As a result, they avoid the problematic scavenging of nitric oxide that is generated from arginine by endothelial nitric oxide synthase. This, along with their ability to deliver oxygen in circulation, supports their potential utility and value as protein-based medicinal targets. However, because proteins have many reactive functional groups, directing a specific coupling reaction to unique sites is a chemical challenge. Furthermore, developing reactions between proteins confronts a significant entropic challenge. The concept and implementation of biorthogonal processes led to the successful application of copper-catalyzed azide-alkyne cycloaddition (CuAAC)(Kolb, et al., Chem., Int. Ed., 2001, 40, 2004-2021) in the formation of useful coupled proteins (Siren, et al., Org. Biomol. Chem., 2015, 13, 10244-10249; Foot, et al., Chem. Commun., 2009, 7315-7317; and Kluger, et al., Chem. Commun., 2010, 46, 1194-1202). For example, the inventors adapted CuAAC to coupling stabilized Hb tetramers using the solubility-directed combination of cross-linked Hb azides and bisalkynes in the presence of Cu(I)(Foot et al., Supra; Y. Yang and R. Kluger, Chem. Commun., 2010, 46, 7557-7559; and Singh et al., Org. Biomol. Chem., 2015, 13, 11118). However, the requirement for Cu(I) can lead to protein denaturation and the ongoing association of protein-bound Cu(I). Subsequent release of copper ions in circulation is then concerning due to its capacity to interfere with cellular processes. Limitations that result from complications associated with CuAAC motivated the inventors to develop an alternative biorthogonal coupling that does not require an added metal ion.

Thus, in some aspects, it would be highly desirable to be provided with an efficient process for producing HBOCs that would not cause vasoconstriction. In addition, the process should not introduce any traces of copper ion.

Still, in some aspect, it would be highly desirable to be provided with HBOCs that would not extravasate through the epithelia, avoiding induced vasoconstriction.

It would also be highly desirable that the HBOCs have an affinity for oxygen that is useful in circulation and perfusion.

BRIEF SUMMARY

The present disclosure concerns a novel approach to the formation of an HBOC such that it forms readily in a state that resists extravasation while providing a suitable oxygenation function.

The present disclosure also concerns a method for producing HBOCs.

According to a first aspect, the present disclosure provides a hemoglobin based oxygen carrier (HBOC) comprising a first hemoglobin protein cross-linked by a strain-promoted alkyne-azide cycloaddition (SPAAC) reaction or a strain-promoted alkyne-nitrone cycloaddition (SPANC) reaction, in absence of copper ions to a second hemoglobin protein, wherein said hemoglobin protein comprises two alpha and 2 beta subunits, said HBOC being capable of binding oxygen and releasing same in a similar manner as in whole blood.

In one embodiment, the first hemoglobin protein comprises hemoglobin covalently linked to an angle strained cycloalkyne moiety and the second hemoglobin protein comprises hemoglobin, the beta subunits of which are covalently linked to an azide or nitrone moiety, wherein the cycloalkyne moiety and the azide or nitrone moiety react together according to the SPAAC or SPANC reaction covalently linking together in a copper-free reaction the first hemoglobin protein to the second hemoglobin protein.

In a further embodiment, the first hemoglobin protein and the second hemoglobin protein, each comprises hemoglobin covalently linked to an "angle-strained" cycloalkyne moiety, the cycloalkyne moiety of the first and second hemoglobin proteins reacting with a compound comprising at least 2 azide moieties or nitrones moieties according to the SPAAC or SPANC reaction covalently linking together in a copper-free reaction the first hemoglobin protein to the second hemoglobin protein.

In an alternate embodiment, there is provided an HBOC comprising a hemoglobin protein comprising hemoglobin covalently linked to azide moieties or nitrone moieties and at least one bulky and non-toxic protein such as albumin, each covalently linked to an angle strained cycloalkyne-containing moiety, the cycloalkyne moiety and each one of said azide moieties or nitrone moieties reacting together to be cross-linked by a strain-promoted alkyne-azide cycloaddition (SPAAC) reaction or a strain-promoted alkyne-nitrone cycloaddition (SPANC) reaction. The purpose of the protein here is to increase the molecular weight of the resulting HBOC to avoid extravasation and scavenging of nitric oxide by smaller molecular weight HBOC containing hemoglobin. As the protein is for human administration, the protein should not be toxic nor cause any undesired side effects.

In preferred embodiments, the angle strained cycloalkyne moiety is a $C_8$-$C_9$ cycloalkyne moiety, such as a cyclooctyne moiety.

In some embodiments, the hemoglobin is deoxyhemoglobin, carbonmonoxyhemoglobin or oxyhemoglobin.

In some embodiments, the cycloalkyne moiety is attached via a chemical cross-link to the beta subunits of the hemoglobin.

In some embodiments, the two beta subunits of each hemoglobin can be cross-linked together. In such a case, amino groups of lysine residues of the beta subunits of each hemoglobin can be cross-linked together.

In some embodiments, the N-terminal residues of the beta subunits of each hemoglobin are cross-linked via their alpha amino groups to amino groups of lysine residues. In such a case, the lysine residues are those preferably located at a position corresponding to amino acid residue 82 or 144 of SEQ ID NO:1.

In some embodiments, the two alpha subunits of each hemoglobin are cross-linked together. In such a case, the lysine residues of the alpha subunits of each hemoglobin can be cross-linked together. Such lysine residues are preferably located at a position corresponding to amino acid residue 99 of SEQ ID NO:2.

In a still further embodiment, there is provided a method for preparing a hemoglobin based oxygen carrier (HBOC) as defined herein. The method comprises the steps of:
  i. providing a first hemoglobin protein comprising hemoglobin covalently linked to an angle strained cycloalkyne moiety;
  ii. providing a second hemoglobin protein comprising hemoglobin, the beta subunits of which are covalently linked to an azide or nitrone moiety; and
  iii. contacting said first and second hemoglobin protein under conditions conducive to a strain-promoted alkyne-azide cycloaddition (SPAAC) reaction or a strain-promoted alkyne-nitrone cycloaddition (SPANC) reaction in absence of copper ions for causing covalent linkage of said first hemoglobin protein to said second hemoglobin protein, resulting in said HBOC.

In another embodiment, there is provided a method for preparing a hemoglobin based oxygen carrier (HBOC) as defined herein. The method comprises the steps of:
  i. producing a first and second hemoglobin protein by covalently linking hemoglobin to an angle strained cycloalkyne moiety; and
  ii. adding a compound comprising at least 2 azide or nitrone moieties for reacting under conditions conducive to a strain-promoted alkyne-azide cycloaddition (SPAAC) reaction or a strain-promoted alkyne-nitrone cycloaddition (SPANC) reaction in absence of copper ions with said first and second hemoglobin protein produced at step i) for causing covalent linkage of said first and second hemoglobin protein to two of said azide or nitrone moieties, resulting in said HBOC.

In another embodiment, there is also provided a composition for use in a method for increasing oxygen transport. The composition comprises the hemoglobin based oxygen carrier (HBOC) as defined herein and a suitable excipient or carrier.

Yet in another embodiment, there is also provided a composition for use in a perfusion. The composition comprises the hemoglobin based oxygen carrier (HBOC) as defined herein and a suitable excipient or carrier.

In a further embodiment, there is also provided a method for providing oxygen transport in vivo in an individual, said method comprising administering intravenously a hemoglobin based oxygen carrier (HBOC) as defined herein, wherein said HBOC is capable of binding oxygen and releasing same in a similar manner as in whole blood.

In another embodiment, there is provided a method for maintaining a tissue or an organ physiologically active, said method comprising the step of perfusing said tissue or organ with a composition comprising the HBOC as defined herein and a suitable excipient or carrier. For example, the composition may also contain a physiologically acceptable saline solution.

In some embodiments, there is provided the use of the HBOC as defined herein for increasing oxygen transport.

In some embodiments, there is also provided the use of the HBOC as defined herein, in a perfusion.

In some embodiments there is also provided for the use of the composition as defined herein for increasing oxygen transport, or in other embodiments, in a perfusion.

BRIEF DESCRIPTION OF THE DRAWINGS

Having thus generally described the nature of the invention, reference will now be made to the accompanying drawings, showing by way of illustration, a preferred embodiment thereof, and in which:

FIG. 1 illustrates the preparation of Hb-cyclooctyne (scheme 1) and Hb-azide (scheme 2).

FIG. 2 illustrates the strain-promoted azide-alkyne cycloaddition (SPAAC) of Hb-cyclooctyne with Hb-azide to produce the hemoglobin bis-tetramer according to a first aspect of the present invention.

DETAILED DESCRIPTION

Figure 3:
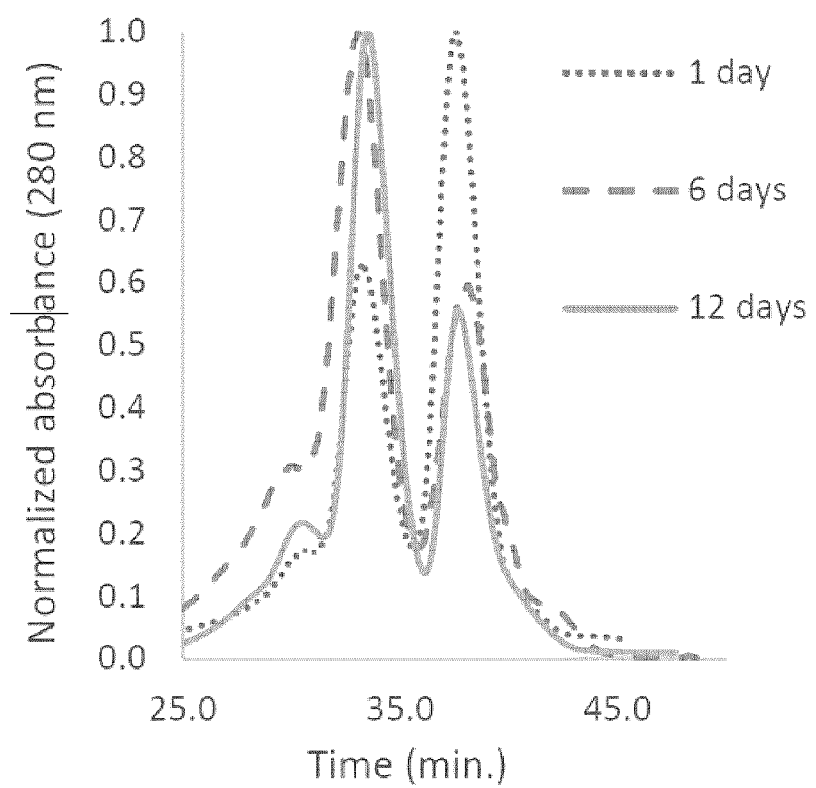
FIG. 3 illustrates a plot of the size-exclusion HPLC trace of the products of the reaction of Hb-cyclooctyne with Hb-azide, the peak at 33 min. being due to the ~128 kDa hemoglobin bis-tetramer and the peak at 38 min. is due to the ~64 kDa cross-linked starting materials.

As used herein, the expression "capable of binding oxygen and releasing same in a similar manner as in whole blood" is meant to refer to the property of the HBOC of the present disclosure that such HBOC would indeed have oxygen carrier capabilities. In fact, the HBOC described herein should be capable of binding oxygen in a high partial pressure of oxygen and to release it at the lower partial pressure of oxygen.

The term Hemoglobin as used herein not only relates without limitation to human adult Hemoglobin A, but also includes any hemoglobin from any source.

The present disclosure concerns a new class of hemoglobin-based oxygen carrier (HBOC) for use as a component of a red cell substitute that is designed to avoid vasoactivity in use, for perfusion or transfusion. To this end, the inventors hypothesized that chemical modifications that increase the overall size of human hemoglobin would prevent vasoconstriction associated with tetramer extravasation and scavenging of nitric oxide (NO). An efficient route to creating a larger species that avoids extravasation is by selective formation of a stable hemoglobin dimer, each hemoglobin comprising its 2 alpha and 2 beta subunits. Using a process investigated by Bertozzi et al. (Agard et al. and Chang et al.) who have shown that cycloalkynes are activated for such a process, presumably by strain that is induced by distortion of their triple bond. The inventors now report that using strain-promoted azide-alkyne cycloaddition (SPAAC) as a metal-free alternative, the inventors can efficiently produce cross-linked Hb bis-tetramers. The preparation of the necessary modified proteins for the cycloaddition process is convenient and the controlled cycloadditions give readily isolable-coupled proteins as products, where each hemoglobin remains functional for binding oxygen and releasing it as natural hemoglobin in the human body would. The HBOC so produced, binds and releases oxygen with moderate affinity and cooperativity, much like native hemoglobin within circulating red blood cells. These materials may serve as red blood cell substitutes in transfusion, in perfusion and for increasing oxygen transport in vivo in an individual.

SPAAC is a metal-free alternative to CuAAC bioconjugation developed, as mentioned above by Bertozzi. The reaction proceeds at room temperature and does not require a catalyst, making it especially useful for the chemical labeling of living systems. The cyclooctyne moieties do not appear to present any in vivo toxicity in mice.

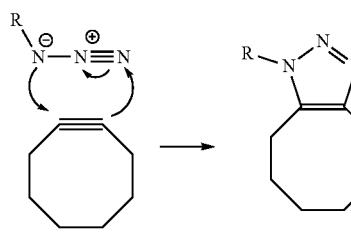

OCT (see below) was the first cyclooctyne substrate developed by Bertozzi. DIBO and DIBAC experience faster kinetics because of the additional $sp^2$ character. Increasing reactivity produces side reactions, exemplified by BARAC, which undergoes hydrolysis in PBS buffer with a half-life of 24 hours. The following compounds are examples of angle strained cycloalkynes.

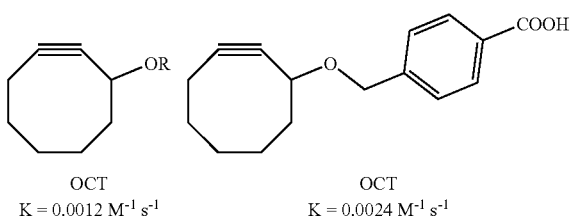

OCT
K = 0.0012 $M^{-1}$ $s^{-1}$

OCT
K = 0.0024 $M^{-1}$ $s^{-1}$

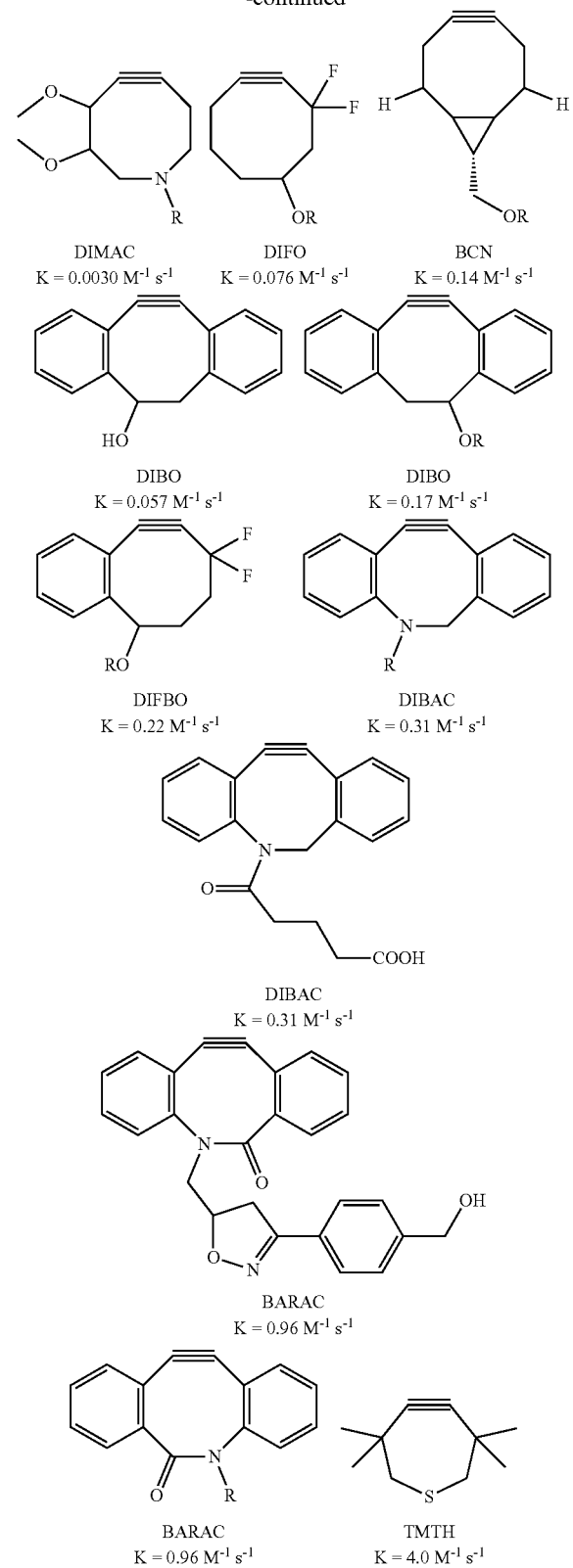

The values of k provided above represents the second order rate constants for reactions of strained cyclooctynes with a common azide. Vladimir Popik (U.S. Pat. No. 8,541,625B2, Org. Biomol. Chem., Oct. 3, 2012, 10(41) 8200-

8202) has designed numerous strained cycloalkynes that could be useful in the present invention.

The SPAAC reaction can proceed without the use of copper ion catalyst due to the ring strain that greatly destabilizes the alkyne, increasing the reaction driving force, and the reactivity of the cycloalkyne to relieve its ring strain.

Ring-strained cycloalkynes or angle-strained cycloalkynes is meant to refer to cycloalkynes bearing a deformation of the R—C≡C bond angle which must occur in order to accommodate the molecular geometry of rings containing less than ten carbons. The strain energies associated with cyclononyne ($C_9H_{14}$) and cyclooctyne ($C_8H_{12}$) are approximately 2.9 kcal/mol and 10 kcal/mol, respectively. This upwards trend in energy for the isolable constituents of this class is indicative of a rapid escalation of angle strain with an inverse correlation to ring size. Analysis by photoelectron spectroscopy has indicated that the alkyne bond in small cyclic systems is composed of two non-degenerate π bonds—a highly reactive strained bond perpendicular to a lower-energy π bond. Cis-bending of the R—C≡C bond angle results in the drastic lowering of the energy of the lowest unoccupied molecular orbital, a phenomenon which accounts for the reactivity of strained cycloalkynes from the perspective of molecular orbital theory.

Cyclooctyne, the smallest isolable cycloalkyne, is able to undergo azide-alkyne Huisgen cycloaddition under mild, physiological conditions in the absence of a copper(I) catalyst due to strain. However, due to ring strain, $C_8$-$C_9$ cycloalkynes, compounds containing same, and their derivatives, can be used in SPAAC reactions.

The inventors with the processes described herein are able to prepare Hb bis-tetramers in the highest yields ever observed using strain-promoted bioorthogonal protein coupling. Combining heme proteins under a carbon monoxide atmosphere in a stable non-denaturing environment ensures a high quality end product that is likely to be suitable for clinical evaluation.

A significant advantage of SPAAC is that linkages between two large proteins in solution can be formed because the reactive moieties remain stable in solution, permitting long reaction times.

Ning et al. (Angew. Chem. Ed. 2010, 49, 3065-3068) have also developed a Copper-free click chemistry adapted to use nitrones as the 1,3-dipole rather than azides and has been used in the modification of peptides. This cycloaddition, sometimes referred to as SPANC for strain-promoted alkyne-nitrone cycloaddition. Such reaction can also be used with success in the present invention.

Both SPAAC and SPANC reactions require a strained cycloalkyne to react without the use of cuprous salts, which once in solution will generate copper ions (as catalyst) with an azide-bearing compound (for SPAAC) or a nitrone-bearing compound (for SPANC). Possible strained cycloalkynes have been mentioned above. As for the possible azide-bearing compounds, for illustrative purpose, without limitation, one may think azide compounds, and compounds having multiple azide moieties available for reaction with an angle strained cycloalkyne moiety, such as diazide compounds, triazide compounds, tetraazide compounds, azide dendrimers, etc. Accordingly, in an embodiment, the HBOC may comprise at least two hemoglobin proteins, each comprising an hemoglobin covalently linked to an angle strained cycloalkyne moiety, said cycloalkyne moiety of each hemoglobin reacting with a corresponding azide moiety of a molecule comprising at least two azide moieties. Examples of Nitrone-bearing compounds useful in a SPAAC reaction can be found amongst others in Ning et al.

In one embodiment, the HBOC comprises species derived from hemoglobin that avoids extravasation, while maintaining the oxygenation function of hemoglobin. The invention also is comprised of the materials derived from covalent linkage of two modified proteins (hemoglobin). The invention provides a method for creating the bis-tetramer assemblies by chemically attaching a cyclooctyne derivative to hemoglobin, then combining the resulting modified protein with hemoglobin modified with a single azide or a small molecule bis-azide. The resulting bis-tetramer assembly is a stable entity that binds and releases oxygen and will minimize any side effects related to blood pressure.

To stabilize the HBOC, the subunits of the hemoglobin can be cross-linked together to prevent dissociation of the subunits, which would cause extravasation and thus vasoconstriction, in addition to causing kidney toxicity. As mentioned above, each subunit of hemoglobin is well-characterized with known sequences. Either the beta subunits, the alpha subunits or both can be cross-linked. For example where the cross-link is between the beta subunits, both beta subunits were modified via epsilon-amino groups of lysine or via the alpha amino group of an N-terminal residue. Preferably, the lysine residue is the one located at a position corresponding to amino acid residue 82 or 144 of SEQ ID NO:1. When the beta subunits are linked together via the alpha amino group of the normal N-terminal valine, it is that which is designated as amino acid residue 1 of SEQ ID NO:1. When the two alpha subunits are linked together, the subunits are preferably cross-linked via the epsilon amino groups of lysine residues, and more preferably the amino group of the lysine residue located at a position corresponding to amino acid residue 99 of SEQ ID NO:2. Various techniques are known for the cross-linking of the alpha subunits or of the beta subunits.

The method for increasing oxygen transport in vivo in an individual preferably comprises the step of administering intravenously a hemoglobin based oxygen carrier (HBOC) as defined herein.

The present invention may be more readily understood by referring to the following examples which are given to illustrate the invention rather than to limit its scope.

EXAMPLE 1

Preparation of Hb-cyclooctyne

A solution of human hemoglobin A (HbA)(Oxygenix Co. Ltd., Tokyo JP) (0.5 mM in 1.5 mL of 50 mM sodium borate buffer, pH 9.0) was oxygenated by stirring under a stream of oxygen with photoirradiation for 2 h at 4° C. The sample was then deoxygenated by stirring under a stream of nitrogen for 2 h at 37° C.

Trimesoyl tris(3,5-dibromosalicylate) (TTDS) (synthesized according to Kluger et al., 1992) was added (2 eq. of a 0.2 M solution in DMSO) and this mixture was stirred for 12 min. Then, amine-cyclooctyne (N-[(1R,8S,9s)-Bicyclo [6.1.0]non-4-yn-9-ylmethyloxycarbonyl]-1,8-diamino-3,6-dioxaoctane) was added (40 eq. of a 1 M solution in DMSO) and the sample was flushed with carbon monoxide. After 1 h of stirring at room temperature, the mixture was passed through a Sephadex™ G-25 column equilibrated with phosphate buffer (0.02 M, pH 7.4). The collected fraction was concentrated by centrifugation through a filter (30 kDa cut-off) and stored under an atmosphere of carbon monoxide at 4° C. The compositions of the products were analyzed by HPLC equipped with a 330 Å C-4 Vydac™ reverse-phase column (4.6 mm×250 mm) and a solvent gradient from 20 to 60% acetonitrile in water spiked with 0.1% trifluoroacetic acid. The eluent was monitored at 220 nm. Slight drifts in retention times were observed because solvents were mixed offline. The identities of the peaks were investigated using electrospray ionization mass spectrometry analysis (AIMS Lab, Department of Chemistry, University of Toronto).

EXAMPLE 2

Preparation of Hb-azide

The procedure is identical to the preparation of Hb-cyclooctyne with the following exceptions: amine-azide (4-azidomethyl-benzylamine) (prepared according to Yang et al., 2010) was added instead of amine-cyclooctyne; the mixture was passed through a G-25 column equilibrated with MOPS buffer (0.1 M, pH 8.0) instead of phosphate buffer. The products were analyzed by reverse-phase HPLC and mass spectrometry as previously described.

EXAMPLE 3

SPAAC of Hb-cyclooctyne with Hb-azide

Hb-cyclooctyne (1 eq., 100 μL of a 0.32 mM stock solution in 0.02 M phosphate buffer, pH 7.4) was combined with Hb-azide (1 eq., 133 μL of a 0.24 mM stock solution in 0.02 M phosphate buffer, pH 7.4) and this mixture was incubated for 12 days at 4° C. under an atmosphere of carbon monoxide. The products were analyzed by HPLC using a Superdex™ G-200 HR size-exclusion column (10 mm×300 mm) and tris-HCl (37.5 mM, pH 7.4) elution buffer containing magnesium chloride (0.5 M). The eluent was monitored at 280 nm.

Human Hb was cross-linked with trimesoyl tris(3,5-dibromosalicylate) (FIG. 1, scheme 1), a trifunctional reagent that reacts with the ε-amino groups of each β-lys-82, leaving the third ester available for further reaction. The polyanionic electrophile reacts site-specifically with residues residing within Hb's cationic funnel that normally associate with 2,3-diphosphoglycerate. Addition of an amine-functionalized hydrocarbon derivative of cyclooctyne to the cross-linked protein ester produces the desired conjugate (Hb-cyclooctyne) (FIG. 1, scheme 1). Addition of an amino azide to the cross-linked protein ester produces an azido conjugate (Hb-azide) (FIG. 1, scheme 2). These derivatives were characterized by reverse-phase HPLC of the product solutions.

Figure 4:
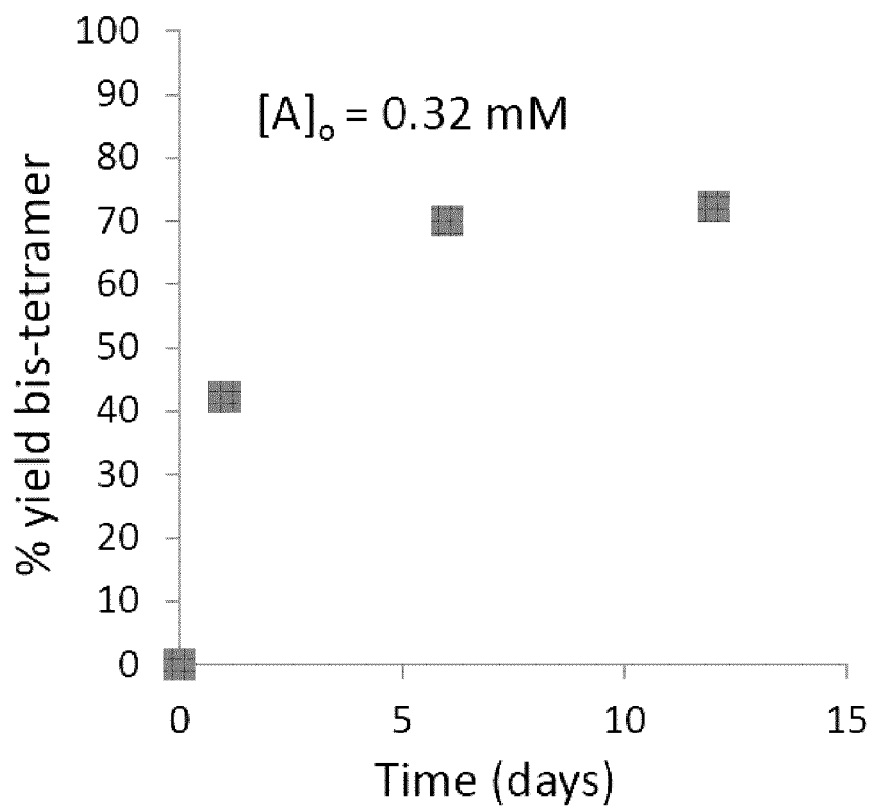
FIG. 4 illustrates a chart reporting the percent yield based on the theoretical maximum.

The cycloaddition of Hb-azide and the Hb-cyclooctyne was initiated by combining solutions of each reactant (FIG. 2). Progress of the reaction was followed by HPLC until an optimal conversion was achieved. After 12 days the reactants were converted in 70% yield to the cycloaddition product, which is a cross-linked bis-tetramer connected by the triazole from the SPAAC process (FIG. 2). Gel electrophoretic analysis confirmed that the peak that elutes earlier than the modified Hb tetramers in the size-exclusion HPLC is the bis-tetrameric species (FIG. 3). Allowing the reaction to proceed for up to 18 more days did not increase the yield (FIG. 4). Other modes of addition and combination of the reactants did not improve the final outcome. Notably, addition of amine-cyclooctyne/azide reagents to CO-Hbs to secure uniformity of the product conformation did not enhance the subsequent SPAAC reaction. The yield increases to 76% by keeping the mixed proteins in their deoxygenated states for four more days. Access to the central channel of the protein is improved in the conformation favored by the deoxy heme. However, this is impractical for a long-term reaction because of the competing formation of non-functional methemoglobin from small amounts of residual oxygen. There was no added benefit neither from heating the solution at 70° C. for 30 min nor by stirring for 12 h at 40° C.

The inventors then assessed the outcome of the SPAAC-based protein-coupling process in comparison to that from CuAAC by coupling a strain-free Hb-alkyne with the Hb-azide in the presence of Cu(I). The alkyne-functionalized tether is comparable in length to amine-cyclooctyne so the inventors chose this to lead to effective coupling. A bathophenanthroline ligand (4 eq.), $CuSO_4$ (2 eq.) and ascorbic acid (40 eq.) were added to the protein mixture. This ratio of reagents has previously been shown to be optimal for the coupling of Hb-azides to bisalkynes. However, with the alkyne covalently tethered to Hb, little product formation occurred. After one hour, only a small fraction of the protein present was coupled. Leaving the reaction mixture longer (greater than one hour) resulted in a significant amount of oxidation of the heme and denaturation of the protein. Methemoglobins were apparent from the deepening colour of the reaction mixture and successive denaturation was confirmed from the observed precipitate. The inventors observed a similar outcome under CuAAC conditions using a Hb-alkyne and a bis-azide. Table 1 below illustrates the yields obtained with the method of the present invention compared to other methods of the prior art. As can be seen, the method of the present invention allows to obtain a 40% yield increase compared to the second best method described by Yang et al.

TABLE 1

Bis-tetramer assembly by SPAAC approach vs. previous methods. Percent yield is the apparent yield calculated from the ratio of bis-tetramer to starting material in the size-exclusion HPLC trace

| Approach % | Yield |
| --- | --- |
| Method described herein | 70 |
| CuAAC (Yang et al.) | 50 |
| CuAAC (Foot et al.) | 20 |
| Aminolysis (Lui et al.) | 40 |

EXAMPLE 4

SPAAC of Hb-cyclooctyne with bis-azide

To Hb-cyclooctyne (1 eq., 100 μL of a 0.32 mM stock solution in 0.02 M phosphate buffer, pH 7.4) was added 0.45 eq. of bis-azide 4,4'-Diazidediphenylsulfone (4.8 μL of a 3 mM stock solution in DMSO) (as synthesized according to Zeng et al., 2013) and this mixture was incubated for 15 days at 4° C. under an atmosphere of carbon monoxide. The products were analyzed by HPLC using a Superdex™ G-200 HR size-exclusion column (10 mm×300 mm) and a Tris-HCl (37.5 mM, pH 7.4) elution buffer containing magnesium chloride (0.5 M). The eluent was monitored at 280 nm.

The bis-tetramer was separated from the reactants by passing the mixture through a Sephadex™ G-100 column equilibrated with Tris-HCl (37.5 mM, pH 7.4) containing magnesium chloride (0.5 M). The first fraction, containing the purified bis-tetramer, was concentrated through a membrane (30 kDa cut-off) and stored under an atmosphere of carbon monoxide at 4° C. The composition of the purified bis-tetramer was evaluated by size-exclusion HPLC as previously described.

Figure 5:
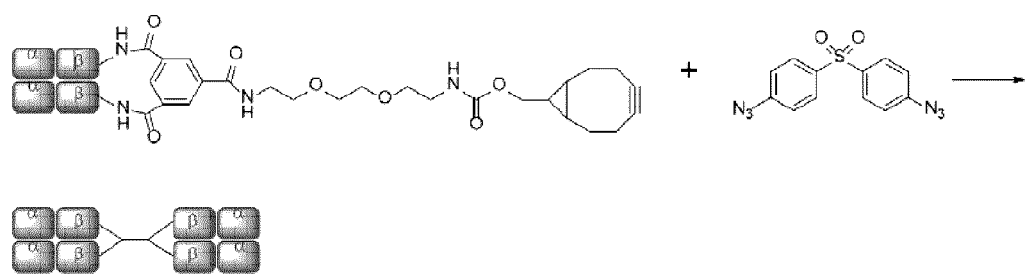
FIG. 5 illustrates the preparation of hemoglobin bis-tetramer by copper-free coupling of Hb-cyclooctyne with bis-azide according to a further aspect of the present invention.
Figure 6:
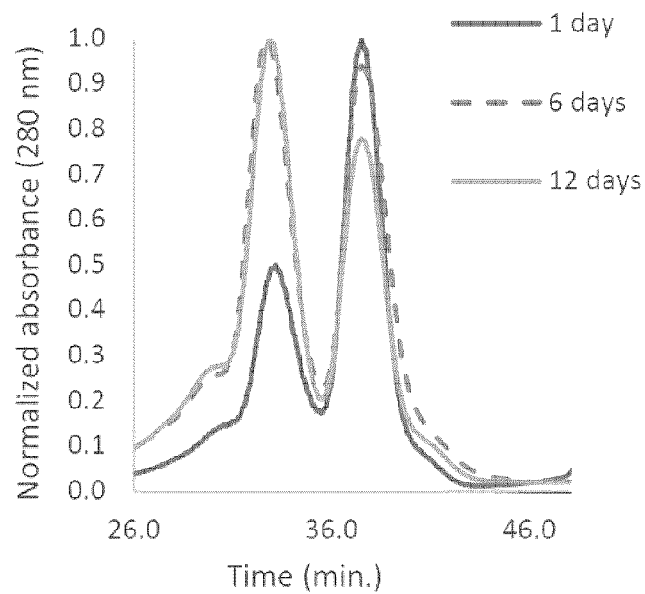
FIG. 6 illustrates the size-exclusion HPLC trace of the products of the reaction of Hb-cyclooctyne with bis-azide, the peak at 33 min. being due to the ~128 kDa hemoglobin bis-tetramer and the peak at 38 min. being due to the ~64 kDa Hb-cyclooctyne starting material.
Figure 7:
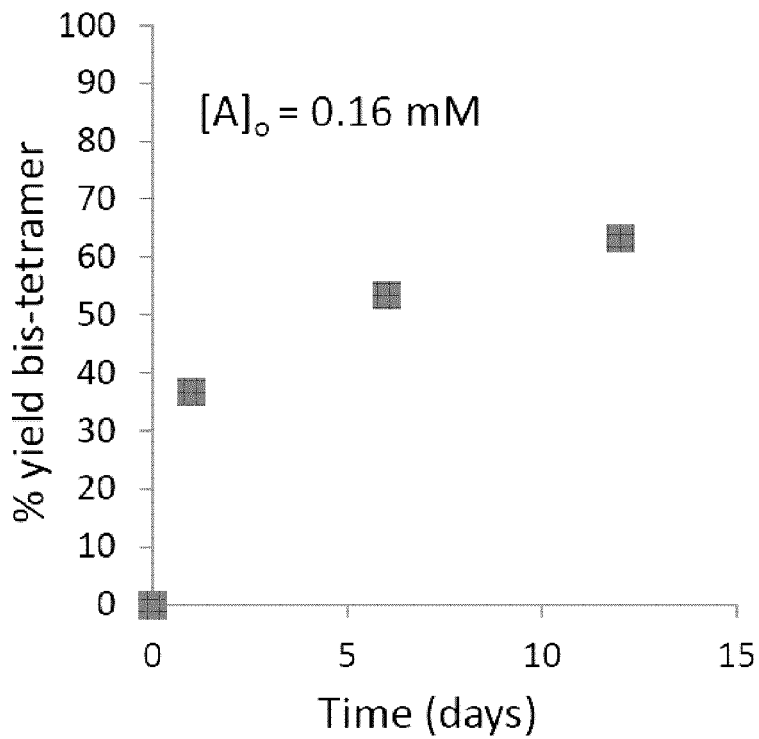
FIG. 7 illustrates the percent yield based on the theoretical maximum.
Figure 8:
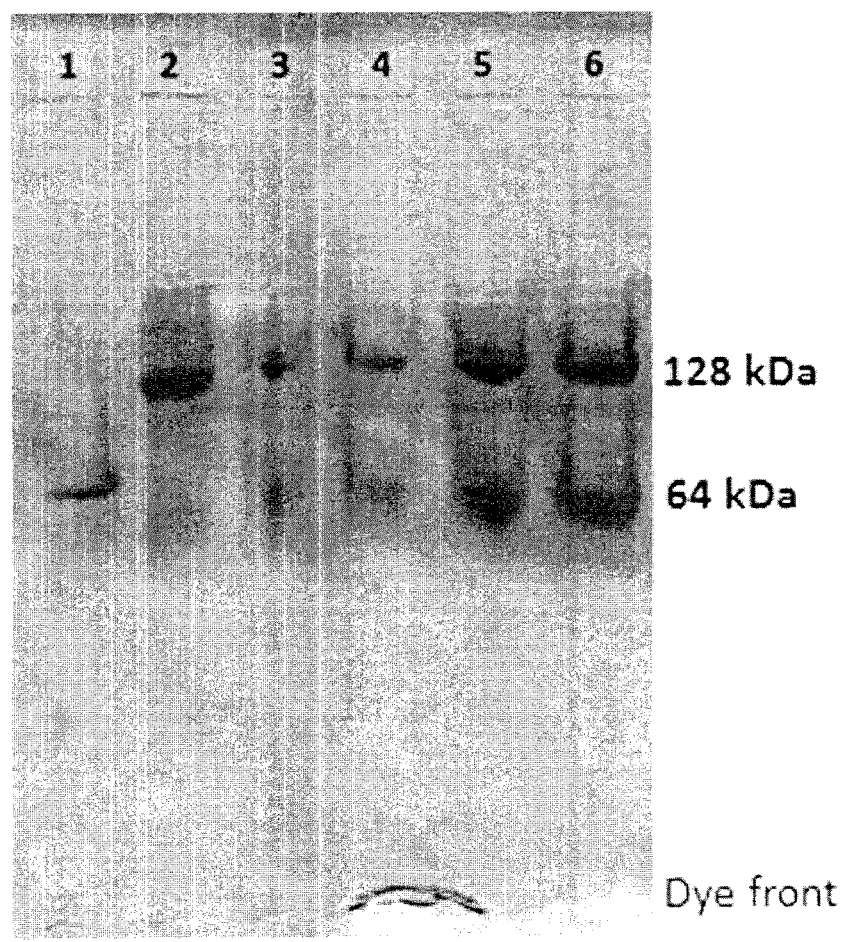
FIG. 8 illustrates the native PAGE analysis of the products of the copper-free click reactions after approximately half the starting material is consumed. Lane 1: Native Hb; Lane 2: Pure Hb bis-tetramer reference; Lanes 3 and 5: Products of the reaction of Hb-cyclooctyne with bis-azide; Lanes 4 and 6: Products of the reaction of Hb-cyclooctyne with Hb-azide.

Despite negative results with other combinations in absence of copper ion (e.g. Hb-alkyne with Hb-azide or bis-azide), Hb-cyclooctyne reacts effectively with a bis-azide (FIG. 5). Approximately 63% bis-tetramer results after incubation at 4° C. for 15 days (FIGS. 6 and 7). The long incubation does not affect the protein in the absence of copper ion and exclusion of oxygen. Native gel electrophoresis analysis revealed that the species eluting first in the size-exclusion HPLC is the bis-tetramer (FIG. 8). The mass spectrum of the product of the reaction of Hb-cyclooctyne with an excess of bis-azide confirms that the bis-azide is capable of reacting with the entire pool of Hb-cyclooctyne. Since every Hb cyclooctyne appendage is accessible to the small molecule bis-azide, then half an equivalent of bis-azide modifies half of the total Hb-cyclooctyne in solution to produce a mixture of approximately 50:50 azido Hb to Hb-cyclooctyne. The yield outcome of the bis-tetramer-forming reaction is then analogous to the combination of the singly modified Hb-azide with the Hb-cyclooctyne noted above. Replacing the rigid bis-azide with an extended linkage derived from condensed ethylene glycols (3,6,9,12,15-pentaoxaheptadecane-1,17-diyl bis-azide) did not improve the outcome, but nevertheless provided a similar outcome. The addition of 2.0 or 10.0 eq. of bis-azide resulted in addition of each azide to no more than one Hb-cyclooctyne in contrast to the reaction with a hydrocarbon bis-alkyne. The alternative strategy in this case would be inefficient due to the complexity of the reagent.

Figure 9:
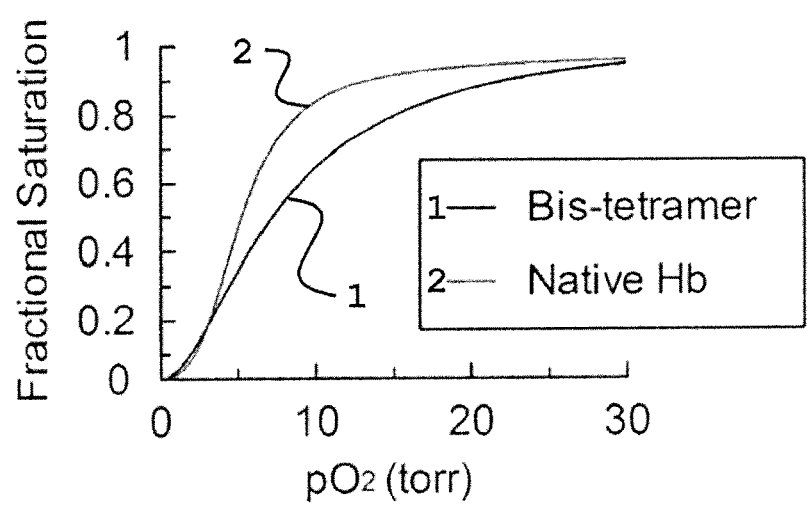
FIG. 9 illustrates the oxygen desaturation curve of the purified bis-tetramer from SPAAC of Hb-cyclooctyne with bis-azide compared to that of native Hb.

The bis-tetramer from SPAAC of Hb-cyclooctyne with bisazide was separated from the reactants prior to the acquisition of its oxygen-binding curve (FIG. 9). The oxygen pressure at half-saturation ($P_{50}$) and the Hill's coefficient of cooperativity at half-saturation ($n_{50}$) of the purified bis-tetramer were determined using a Hemox Analyzer™ with the sample maintained at 27° C. These conditions were optimized for laboratory measurements and not as a model for circulatory studies. Hb samples (5 mL, 0.013 M), prepared in phosphate buffer (0.01 M, pH 7.4), were oxygenated prior to analysis by stirring under a stream of oxygen with photoirradiation for 1.5 h at 4° C. The sample was then contained in a cell connected to the Hemox Analyzer™ for acquisition of the oxygen desaturation curve. The conversion to the deoxy state was achieved by flushing the cell with nitrogen. The data were fitted to the Adair equation using computation of a best fit by the method of non-linear least squares.

The oxygen affinity of the purified bis-tetramer ($P_{50}$=8.1±0.3 torr) is similar to that of native Hb ($P_{50}$=5 torr) and the cooperativity remains significant in the bis-tetramer ($n_{50}$=2.0±0.1). These oxygen binding properties are comparable to those previously reported by Lui et al. (2012) and Yang et al. (2010) for bis-tetramers with structurally analogous features.

EXAMPLE 5

Native Gel Electrophoresis

The 2-Dimensional Tris-HCl polyacrylamide gels contained 12% separating gel (pH 8.8) and 4% stacking gel (pH 8.8). Sample buffer was adjusted to pH 6.8 and running buffer to pH 8.3. The finished gels were stained with Coomassie Brilliant Blue. PAGE followed standard operation as described in Arndt et al. (2012).

EXAMPLE 6

Preparation of Hb-DIBO and Hb-Exclusive Clusters

Building on the afore-mentioned advantages of SPAAC, the inventors then sought to assemble higher order structures of Hb and albumin using as small an excess of the proteins as possible. The previously reported Hb-albumin cluster (HemoAct) requires purification from excess albumin and must also be separated from partially modified species. Using SPAAC as a protein-clustering tool, the inventors combined a specifically derivatized Hb with complementary shielding proteins in a quantitative manner to minimize the need for post-production protein purification.

Figure 10:
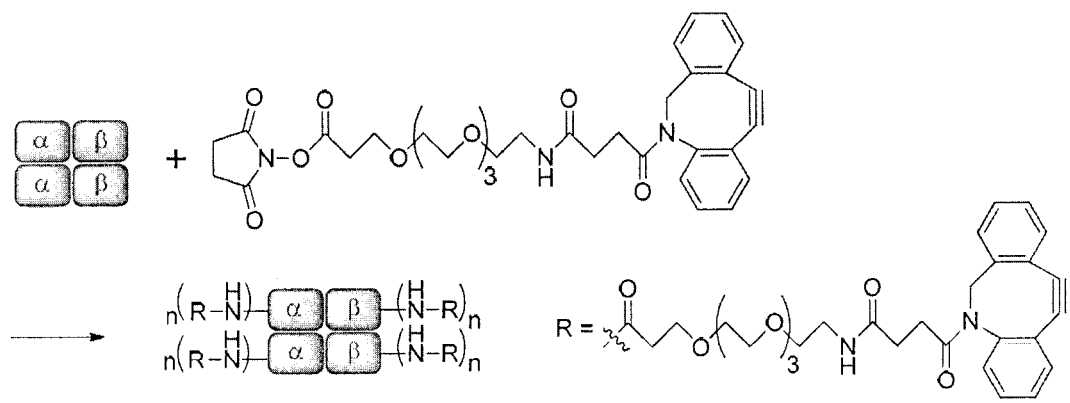
FIG. 10 illustrates the decoration of native Hb with NHS-DIBO to give Hb-DIBO. The number of cyclooctynes appended per Hb subunit (n) could not be determined by mass spectrometry analysis.

A variety of possible cluster architectures were prepared before the final optimized assembly was realized. Initially, the inventors wished to shield the central oxygen carrying protein with cross-linked Hb derivatives to maximize the oxygen-carrying capacity of the overall structure. The inventors were successful in appending multiple cross-linked Hb-azide derivatives to a core protein with conjugates of multiple dibenzocyclooctyne moieties. Hb (non-cross-linked and β-subunit cross-linked) was non-specifically acylated with NHS-DIBO (dibenzocyclooctyne) to give Hb-DIBO/xlHb-DIBO, respectively (FIG. 10). The reverse-phase HPLCs of these products reveal the impact that this modification has on the surface character of the protein. Addition of non-polar appendage to Hb rendered the surface hydrophobic such that most of the protein elutes very late and non-separated. Mass spectral analysis of the fractions collected from reverse-phase HPLC proved to be challenging; the inventors assume that 1-3 cyclooctynes are appended per subunit based on the pattern of modification of Hb with the NHS-alkyne.

Figure 11:
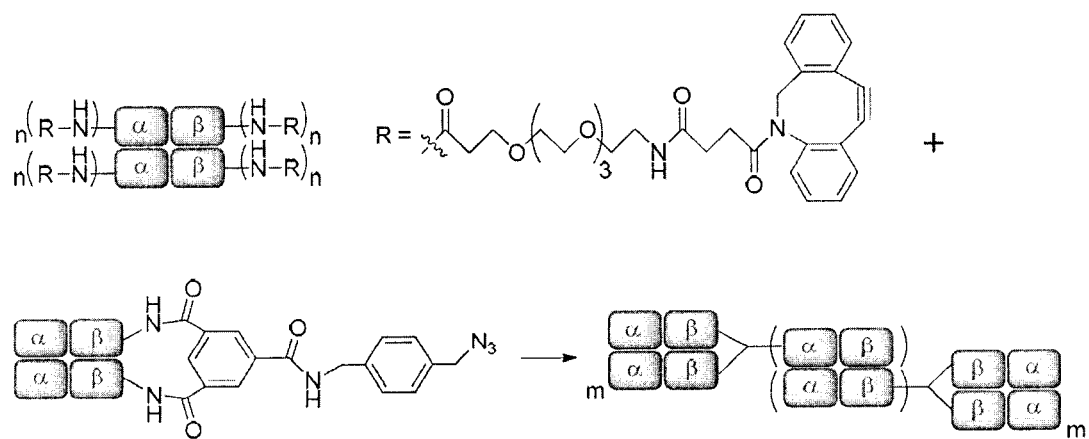
FIG. 11 illustrates the copper-free click of Hb-DIBO with Hb-azide. The number of cyclooctynes appended per Hb subunit (n) could not be determined by mass spectrometry analysis. The number of cross-linked tetramers per Hb dimer (m)=1 to 2.
Figure 12:
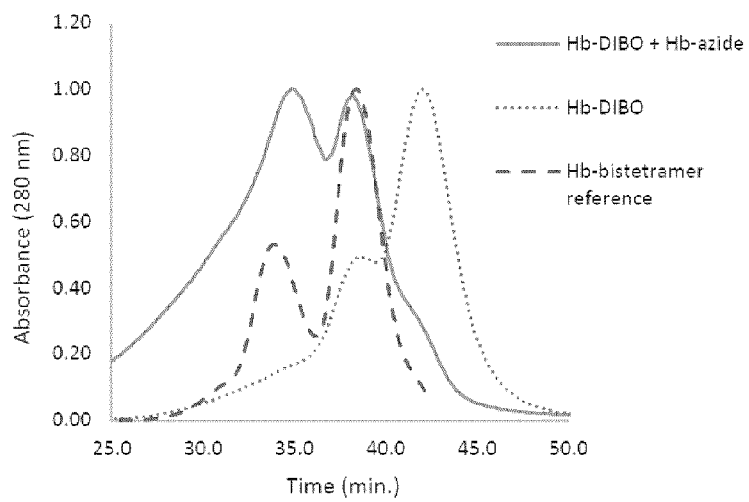
FIG. 12 illustrates the size-exclusion HPLC trace under high salt conditions of the products of the copper-free click of Hb-DIBO with Hb-azide. The (impure) Hb bis-tetramer reference (~128 kDa) elutes at 34 min. while cross-linked starting material (~64 kDa) elutes at 38 min. Hb αβ dimer (~32 kDa) elutes at 41 min.
Figure 13:
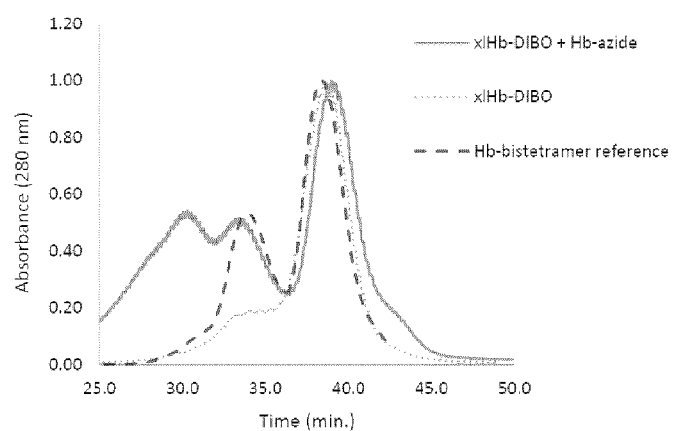
FIG. 13 illustrates the size-exclusion HPLC trace under high salt conditions of the products of the copper-free click of xlHb-DIBO with Hb-azide. The (impure) Hb bis-tetramer reference (~128 kDa) elutes at 34 min. while cross-linked starting material (~64 kDa) elutes at 38 min.

Hb-DIBO/xlHb-DIBO was combined with Hb-azide to give the product proposed in FIG. 11. Size-exclusion HPLC analysis of the Hb-DIBO/Hb-azide product under high salt conditions (FIG. 12) reveals that the reaction proceeds to near completion in one day at 4° C. The very small amount of the 32 kDa αβ dimer peak suggests that Hb-cyclooctyne is appended to at least two Hb-azide tetramers. This geometry maximizes the shielding of the central tetramer and ensures that each dimer is affixed to a larger structure. Products with either one or two tetramers linked to the central scaffold were obtained when xlHb-DIBO was the substrate (FIG. 13).

Native gel analysis confirmed the identities of the peaks in size-exclusion HPLC. In both ensembles (incorporating Hb-DIBO or xlHb-DIBO), bands due to the ~128 kDa bis-tetramer and a higher molecular weight species are visible, which as can be assumes is an ensemble formed from three Hbs.

SPAAC assembly of Hb clusters is advantageous because the many surface-accessible strained moieties in conjunction with the inherent enhanced reactivity of dibenzocyclooctynes compared to cyclooctynes ensures the rapid and complete functionalization of Hb. Additional shielding groups and useful small molecules should also be appended to the remaining reactive groups. However, the inventors sought to simplify the procedure further by avoiding production of cross-links.

Figure 14:
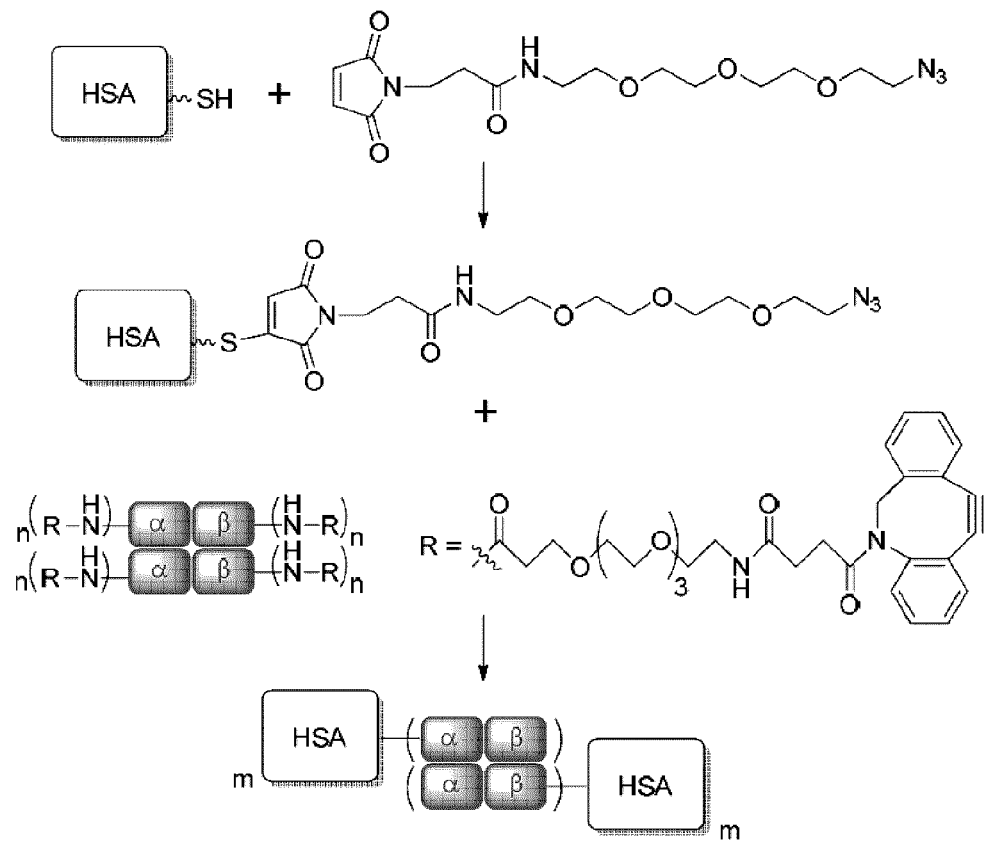
FIG. 14 illustrates the SPAAC of Hb-DIBO with albumin-azide. The number of cyclooctynes per Hb subunit (n) could not be determined by mass spectrometry analysis. The number of albumin proteins per Hb dimer (m)=1 to 3 based on the size exclusion HPLC.
Figure 15:
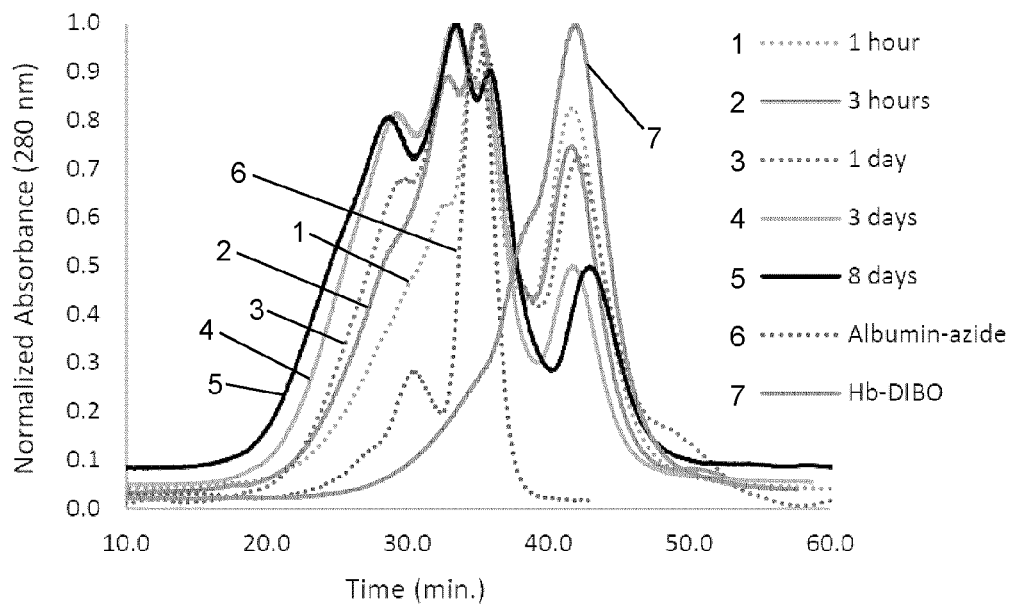
FIG. 15 illustrates the size-exclusion HPLC trace under high salt conditions of the products of the reaction between albumin-azide and Hb-DIBO (3 equiv albumin to 1 equiv Hb). Peaks are as follows: 28 min. (αβ dimer+2×albumin), 33 min. (αβ dimer+1×albumin), 35 min. (albumin), 41 min. (αβ dimer).
Figure 16:
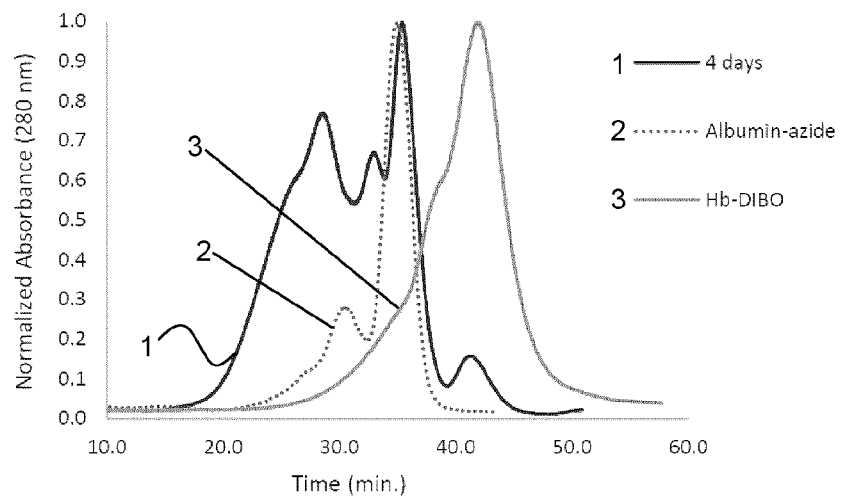
FIG. 16 illustrates the size-exclusion HPLC trace under high salt conditions of the products of the reaction between albumin-azide and Hb-DIBO (6 equiv albumin to 1 equiv Hb). Peaks are as follows: 28 min. (αβ dimer+2×albumin), 33 min. (αβ dimer+1×albumin), 35 min. (albumin), 41 min. (αβ dimer).

Substitution of Hb-azide with the non-vasoactive 67 kDa albumin is the logical solution (FIG. 14). Albumin is a major constituent of blood plasma at a normal concentration of 4 g/dL. Cys-34 residues that were not blocked by post-translational cysteinylation were modified with maleimide-azide, which is unstable and must be prepared from azido-PEG3-amine and maleimide-NHS-ester. The partial purity of the product albumin-azide was assessed based on analysis by mass spectrometry. Nonetheless, Hb-albumin clusters can be prepared by this method. It is noted that a single αβ dimer within the tetramer can accommodate up to at least two albumin proteins. The major peaks seen in the size-exclusion HPLC at 28 min. and 33 min. and are due to (αβ dimer+one albumin) and (αβ dimer+two albumins), respectively (see FIGS. 15 and 16). Constructs of albumin-azide and Hb-cyclooctyne were also prepared.

Figure 17:
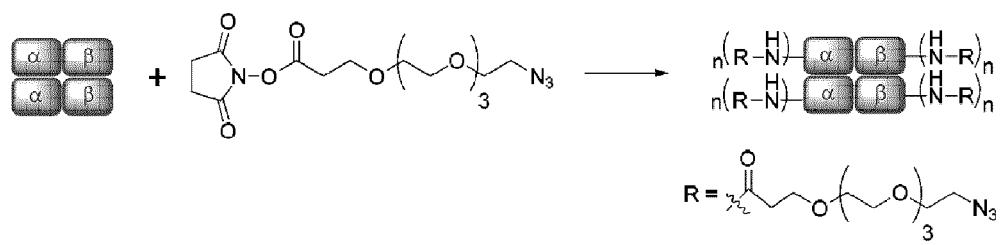
FIG. 17 illustrates the preparation of Hb-PEG-azide by treatment of native Hb with NHS-azide. The number of azides appended per Hb subunit (n)=1 to 6.

Although Hb-DIBO and albumin-azide did readily combine, it was not possible to exert complete control over the outcome of the reaction using a heterogeneous and undefined albumin-azide starting material. It was by reversing the modification scheme and functionalizing the surface of Hb with azides that the inventors were able to produce the highest value product. First, native Hb in the carbon monoxide bound state was reacted with the small molecule NHS-azide (FIG. 17). The protein surface of the resultant Hb-PEG-azide is significantly less hydrophobic than that of Hb-DIBO based on the elution pattern of the reverse-phase HPLC.

Figure 18:
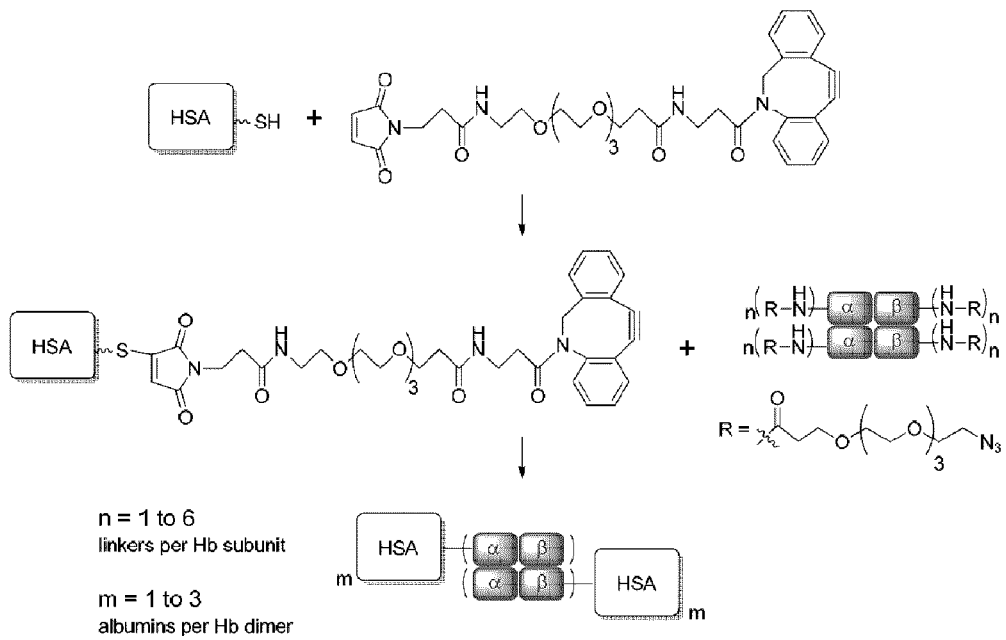
FIG. 18 illustrates the SPAAC of Hb-PEG-azide with albumin-DIBO to assemble the Hb-albumin cluster.

Albumin-DIBO was prepared as the complementary reactive partner and combined with Hb-PEG-azide (FIG. 18). Unlike albumin-azide, albumin-DIBO is a well-defined starting material and is well characterized by mass spectrometry. It is apparent from the mass spectrum of albumin-DIBO that the cysteinylated albumin portion is not modified by the reagent at the surface accessible residue. Therefore, only approximately half of the total albumin participates in SPAAC. Cysteinylated albumin can be stabilized in the reduced form by careful chemical treatment, but the inventors decided to work with the protein as is because the minor non-vasoactive contamination should not have an adverse effect in vivo. The inventors were able to fully modify Hb-PEG-azide using a small excess of albumin-DIBO. Complete modification is defined by addition of at least one albumin to each αβ dimer within the tetramer so that the dissociated construct exceeds the size threshold for renal filtration and extravasation. Based on the size exclusion HPLC, a maximum of three albumin proteins adhere to one αβ-dimer within the overall tetramer. The utility of SPAAC to bring together large proteins without competition by hydrolysis or denaturation is a significant advantage of this approach. The Hb-albumin cluster of Hosaka et al. that is assembled using SMCC (succinimidyl 4-(N-maleimidomethyl)cyclohexane-1-carboxylate) requires purification from a large excess of albumin. In the present method, only a small excess of albumin is present. Therefore, this material could be tested as an oxygen carrier immediately without further purification.

In assembling a product with a predictable composition by a method that is both simple and direct, the inventors prepared a product with high therapeutic potential. Assembly of Hb-albumin clusters using SPAAC as the primary synthetic tool to bring together large proteins has several advantages over competitive preparations: 1) The protein is manipulated exclusively in the stable CO-bound state; 2) There is no risk of potentially vasoactive contaminants; 3) Wasted byproducts are minimized 4) The material can be used as an oxygen carrier immediately without further purification; and 5) The composition is defined so that the physiological outcomes will be related to consistent materials.

Figure 19:
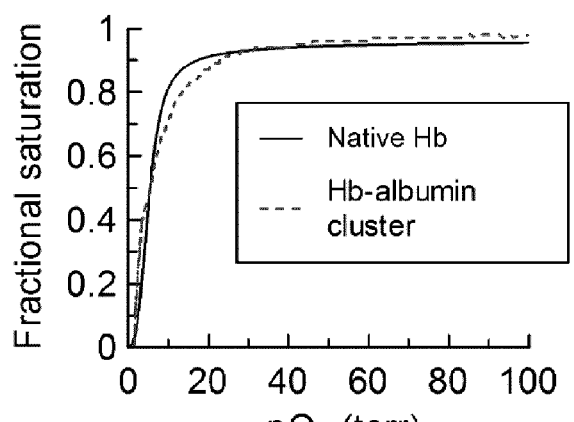
FIG. 19 illustrates the oxygen binding curve of Hb-albumin cluster prepared from combination of Hb-PEGazide with albumin-DIBO.

The material modified to completion by albumin-azide was analyzed for oxygen binding without purification. The product mixture yields a heterogeneous binding curve with an oxygen affinity similar to that of native hemoglobin ($P_{50}$=6.2+/−0.4) and moderate cooperativity ($n_{50}$=1.5+/−0.1) (FIG. 19).

SPAAC provides a practical and convenient route for the precise coupling and clustering of heme proteins. Metal free 'click' chemistry ensures that the heme is not harmed by the reaction conditions. Bis-tetramers can be constructed efficiently either by coupling bioorthogonally modified proteins directly or by linking tetramers via a small molecule bis-azide bridge. The architecture of two coupled Hb tetramers cross-linked between the β-subunits should support safe and effective oxygen delivery. Hb-albumin clusters are a readily accessible alternative that can be prepared by shielding the central protein with neighboring accessory proteins. The improved approached is enticing for its large scale manufacturing potential. The protein therapeutic would be assembled by a synthetic sequence that converts raw materials directly to the final product with minimal complexity. Considering the simplicity of the preparation and the high quality of the product, we expect that these innovations will translate readily to industrial scale-up.

Preparation of Hb-DIBO and Hb-Exclusive Clusters

To native Hb (0.1 mM in 1.6 mL of PBS buffer, pH 7.4) was added NHS-DIBO (30 µL of a 100 mM solution in DMSO). This mixture was stirred for 2 h at room temperature then passed through a Sephadex™ G-25 column equilibrated with 0.02 M phosphate buffer, pH 7.4. The collected fraction was concentrated by centrifugation through a filter (30 kDa cut-off) and stored under an atmosphere of carbon monoxide at 4° C. The same procedure was followed to modify β-subunit cross-linked ($\alpha_2\beta$82-trimesoyl-β82) Hb to give xlHb-DIBO. The products were analyzed by reverse-phase HPLC and mass spectrometry.

Hb-DIBO/xlHb-DIBO (1 eq., 62 µL of a 0.1 mM stock solution in 0.02 M phosphate buffer, pH 7.4) and Hb-azide (approx. 4 eq. of a 0.62 mM stock solution in 0.02 M phosphate buffer, pH 7.4) were incubated together for 1 day at 0° C. under an atmosphere of carbon monoxide. The products were analyzed by size-exclusion HPLC.

Preparation of Albumin-Azide

The azido-PEG3-amine (1.1 eq., oil) was dissolved in 1 mL DMSO and this solution was added to the maleimide NHS-ester (1 eq., solid). The mixture was stirred for 30 min. at room temperature then added it directly to albumin (the reagent must be made fresh). The maleimide-azide (30 eq., 24 µmol, 0.32 mL of a 75 mM maleimide-azide solution in 1 mL DMSO) was added to albumin (1 eq., 0.79 µmol, 0.15 mM solution in 5.24 mL 50 mM phosphate buffer, pH 6.5). This mixture was stirred for 2 h at room temperature. The solution was diluted to 15 mL with 0.02 M phosphate buffer, pH 7.4 then concentrated by centrifugation through a filter (30 kDa cut-off). This process was repeated 3 times. The albumin-azide was stored in the fridge at 4° C. The concentration of the stock solution was determined using the extinction coefficient of HSA at 280 nm of 36500 $M^{-1}$ $cm^{-1}$. The whole protein was submitted to mass spectrometry analysis.

Preparation of Hb-Albumin Cluster from Albumin-Azide

Hb-DIBO (1 eq., 0.008 µmol, 100 µL of a 0.08 mM stock solution in 0.02 M phosphate buffer, pH 7.4) was added to albumin-azide (approx. 4 eq. of a 0.23 mM stock solution in 0.02 M phosphate buffer, pH 7.4). The final volume of the solution was adjusted to 100 µL by concentration through a filter (30 kDa cut-off). The mixture was stirred at room temperature under an atmosphere of carbon monoxide for 2 h then incubated at 4° C. for ~1 week. The products were analyzed by size-exclusion HPLC. Clusters were also prepared using ~8 eq. of albumin.

Preparation and SPAAC of Hb-PEG-azide and Albumin-DIBO

The procedure for the preparation of Hb-PEG-azide is identical to the preparation of Hb-DIBO except NHS-DIBO was replaced with NHS-azide. Briefly, to native Hb (0.1 mM in 1.6 mL of PBS buffer, pH 7.4) was added NHS-DIBO (30 µL of a 100 mM solution in DMSO). This mixture was stirred for 2 h at room temperature then passed through a Sephadex G-25 column equilibrated with 0.02 M phosphate buffer, pH 7.4. The collected fraction was concentrated by centrifugation through a filter (30 kDa cut-off) and stored under an atmosphere of carbon monoxide at 4° C. The same procedure was followed to modify β-subunit cross-linked (α2β82-trimesoyl-β82) Hb to give xlHb-DIBO. The products were analyzed by reverse-phase HPLC and mass spectrometry as previously described.

The procedure for the preparation of albumin-DIBO is identical to the preparation of albumin-azide except maleimide-azide was replaced with maleimide-DIBO. Briefly, maleimide-DIBO (30 eq., 24 µmol, 0.32 mL of a 75 mM solution in DMSO) was added to albumin (1 eq., 0.79 µmol, 0.15 mM solution in 5.24 mL 50 mM phosphate buffer, pH 6.5). This mixture was stirred for 2 h at room temperature. The solution was diluted to 15 mL with 0.02 M phosphate buffer, pH 7.4 then concentrated by centrifugation through a filter (30 kDa cut-off). This process was repeated three times. The resulting albumin-DIBO was stored in the fridge at 4° C. The concentration of the stock solution was determined using the extinction coefficient of HSA at 280 nm ($36500 M^{-1} cm^{-1}$). The whole protein was submitted to mass spectrometry analysis.

The procedure for SPAAC of Hb-PEG-azide with albumin-DIBO is identical to SPAAC of Hb-DIBO with albumin-azide except Hb-DIBO was replaced with Hb-PEG-azide and albumin azide was replaced with albumin-DIBO. Briefly, albumin-DIBO (3 eq., 0.042 µmol, 24.3 µL of a 1.71 mM stock solution in 0.02 M phosphate buffer, pH 7.4) was added to Hb-PEG-azide (0.014 µmol, 25 µL of a 0.56 mM stock solution in 0.02 M phosphate buffer, pH 7.4). The mixture flushed with carbon monoxide and incubated at 4° C. for 3 days. The products were analyzed by size-exclusion HPLC as previously described.

While the invention has been described in connection with specific embodiments thereof, it will be understood that the scope of the claims should not be limited by the preferred embodiments set forth in the examples, but should be given the broadest interpretation consistent with the description as a whole.

REFERENCES

Abel, G. R., Z. A. Calabrese, J. Ayco, J. E. Hein and T. Ye, Bioconjugate Chem., 2016, 27, 698-704.

Agard, N. J., J. A. Prescher and C. R. Bertozzi, J. Am. Chem. Soc., 2004, 126, 15046-15047.

Alagic, A., A. Koprianiuk and R. Kluger, J. Am. Chem. Soc., 2005, 127, 8036-8043.

Arndt, C., S. Koristka, H. Bartsch and M. Bachmann, in Protein Electrophoresis, ed. B. T. Kurien and R. H. Scofield, Humana Press, 2012, vol. 869, ch. 5, pp. 49-53.

Baskin, J. M., J. A. Prescher, S. T. Laughlin, N. J. Agard, P. V. Chang, I. A. Miller, A. Lo, J. A. Codelli and C. R. Bertozzi, Proc. Natl. Acad. Sci. U. S. A., 2007, 104, 16793-16797.

Buehler, P. W., D'Agnillo, F., and Schaer, D. J. Hemoglobin-based oxygen carriers: from mechanisms of toxicity and clearance to rational drug design, Trends in Molecular Medicine 16, 447-457.

Caccia, D., Ronda, L., Frassi, R., Perrella, M., Del Favero, E., Bruno, S., Pioselli, B., Abbruzzetti, S., Viappiani, C., and Mozzarelli, A. (2009) PEGylation Promotes Hemoglobin Tetramer Dissociation, Bioconjugate Chemistry 20, 1356-1366.

Chang, P. V., J. A. Prescher, E. M. Sletten, J. M. Baskin, I. A. Miller, N. J. Agard, A. Lo and C. R. Bertozzi, Proc. Natl. Acad. Sci. U. S. A., 2010, 107, 1821-1826.

Chen, J.-Y. et al., ., Scerbo, M., and Kramer, G. (2009) A Review of Blood Substitutes: Examining The History, Clinical Trial Results, and Ethics of Hemoglobin-Based Oxygen Carriers, Clinics (Sao Paulo, Brazil) 64, 803-813.

Deroo, S., Stengel, F., Mohammadi, A., Henry, N., Hubin, E., Krammer, E. M., Aebersold, R. and Raussens, V., ACS Chem. Biol., 2015, 10, 1010-1016.

Desfougeres, Y., Croguennec, T., Lechevalier, V., Bouhallab, S., and Nau, F. (2010) Charge and Size Drive Spontaneous Self-Assembly of Oppositely Charged Globular Proteins into Microspheres, The Journal of Physical Chemistry B 114, 4138-4144.

Foot, J. S., Lui, F. E., and Kluger, R. (2009) Hemoglobin bis-tetramers via cooperative azide-alkyne coupling, Chemical Communications, 7315-7317.

Gaetke, L. M. and C. K. Chow, Toxicology, 2003, 189, 147-163.

Green, N. M. (1970) Spectrophotometric determination of avidin and biotin, In Methods in Enzymology, pp 418-424, Academic Press.

Gruttner, C., K. Muller and J. Teller, IEEE Trans. Magn., 2013, 49, 172-176.

Guarnone, R., Centenara, E., and Barosi, G. (1995) Performance characteristics of Hemox-Analyzer for assessment of the hemoglobin dissociation curve, Haematologica 80, 426-430.

Guillochon, D., Vijayalakshmi, M. W., Thiam-Sow, A., Thomas, D., and Chevalier, A. (1986) Effect of glutaraldehyde on hemoglobin: functional aspects and Mossbauer parameters, Biochemistry and Cell Biology 64, 29-37.

Harris, D. R., and Palmer, A. F. (2008) Modern Cross-linking Strategies for Synthesizing Acellular Hemoglobin-Based Oxygen Carriers, Biotechnology progress 24, 1215-1225.

Haruki, R., Kimura, T., Iwasaki, H., Yamada, K., Kamiyama, I., Kohno, M., Taguchi, K., Nagao, S., Maruyama, T., Otagiri, M., and Komatsu, T. (2015) Safety Evaluation of Hemoglobin-Albumin Cluster "HemoAct" as a Red Blood Cell Substitute, Scientific Reports 5, 12778.

Hong, V., S. I. Presolski, C. Ma and M. G. Finn, Angew. Chem., Int. Ed., 2009, 48, 9879-9883.

Hu, D. and Kluger, R., Biochemistry, 2008, 47, 12551-12561.

Jonathan, S. J., Arezou Sadighi, A., and Randall, J. H. (2012) Cross-linked, Polymerized, and PEG-Conjugated Hemoglobin-Based Oxygen Carriers: Clinical Safety and Efficacy of Recent and Current Products, Current Drug Discovery Technologies 9, 158-165.

Kim-Shapiro, D. B., A. N. Schechter and M. T. Gladwin, Arterioscler., Thromb., Vasc. Biol., 2006, 26, 697-705.

Kluger, R. and Y. Song, J. Org. Chem., 1994, 59, 733-736.

Kluger, R. and Alagic, A., Bioorg. Chem., 2004, 32, 451-472.

Kluger, R., J. S. Foot and A. A. Vandersteen, Chem. Commun., 2010, 46, 1194-1202.

Kluger, R., Song, Y., Wodzinska, J., Head, C., Fujita, T. S., and Jones, R. T. (1992) Trimesoyltris(3,5-dibromosalicylate): specificity of reactions of a trifunctional acylating agent with hemoglobin, Journal of the American Chemical Society 114, 9275-9279.

Kluger, R., Wodzinska, J., Jones, R. T., Head, C., Fujita, T. S., and Shih, D. T. (1992) Three-point cross-linking: potential red cell substitutes from the reaction of trimesoyl tris(methyl phosphate) with hemoglobin, Biochemistry 31, 7551-7559.

Kolb, H. C., M. G. Finn and K. B. Sharpless, Angew. Chem., Int. Ed., 2001, 40, 2004-2021.

Liljestrom, V., Mikkilä, J., and Kostiainen, M. A. (2014) Self-assembly and modular functionalization of three-dimensional crystals from oppositely charged proteins, Nat Commun 5.

Livnah, O., Bayer, E. A., Wilchek, M., and Sussman, J. L. (1993) Three-dimensional structures of avidin and the avidin-biotin complex, Proceedings of the National Academy of Sciences of the United States of America 90, 5076-5080.

Lui, F. E. and Kluger, R., Biochemistry, 2009, 48, 11912-11919.

Lui, F. E., Dong, P., and Kluger, R. (2008) Polyethylene Glycol Conjugation Enhances ite Reductase Activity of Native and Cross-Linked Hemoglobin, Biochemistry 47, 10780.

Lui, F. E., Yu, B., Baron, D. M., Lei, C., Zapol, W. M., and Kluger, R. (2012) Hemodynamic responses to a hemoglobin bis-tetramer and its polyethylene glycol conjugate, Transfusion 52, 974-982.

Mozzarelli, A., Ronda, L., Faggiano, S., Bettati, S., and Bruno, S. (2010) Haemoglobin-based oxygen carriers: research and reality towards an alternative to blood transfusions, Blood Transfusion 8, s59-s68.

Ning et al., Angew. Chem. Ed. 2010, 49, 3065-3068.

Ornelas, C., J. Broichhagen and M. Weck, J. Am. Chem. Soc., 2010, 132, 3923-3931.

Petronzelli, F., Pelliccia, A., Anastasi, A. M., Lindstedt, R., Manganello, S., Ferrari, L. E., Albertoni, C., Leoni, B., Rosi, A., D'Alessio, V., Deiana, K., Paganelli, G., and De Santis, R. (2010) Therapeutic Use of Avidin Is Not Hampered by Antiavidin Antibodies in Humans, Cancer Biotherapy and Radiopharmaceuticals 25, 563-570.

Ramil and Lin Chem Commun 2013, 49 11007-11022

Repo, S., Paldanius, T. A., Hytönen, Vesa P., Nyholm, T. K. M., Hailing, Katrin K., Huuskonen, J., Pentikäinen, Olli T., Rissanen, K., Slotte, J. P., Airenne, T. T., Salminen, T. A., Kulomaa, Markku S., and Johnson, Mark S. (2006) Binding Properties of HABA-Type Azo Derivatives to Avidin and Avidin-Related Protein 4, Chemistry & Biology 13, 1029-1039.

Rifkind, J. M., L. D. Lauer, S. C. Chiang and N. C. Li, Biochemistry, 1976, 15, 5337-5343.

Schiffner, T., N. de Val, R. A. Russell, S. W. De Taeye, A. T. De la Pena, G. Ozorowski, H. J. Kim, T. Nieusma, F. Brod, A. Cupo, R. W. Sanders, J. P. Moore, A. B. Ward and Q. J. Sattentau, J. Virol., 2016, 90, 813-828.

Schoffelen, S., J. Beekwilder, M. F. Debets, D. Bosch and J. C. M. V. Hest, Bioconjugate Chem., 2013, 24, 987-996.

Schumacher, M. A., Dixon, M. M., Kluger, R., Jones, R. T. and Brennan, R. G., Nature, 1995, 375, 84-87.

Singh, S., I. S. Dubinsky-Davidchik, Y. Yang and R. Kluger, Org. Biomol. Chem., 2015, 13, 11118.

Sinz, A., C. Arlt, D. Chorev and M. Sharon, Protein Sci., 2015, 24, 1193-1209.

Siren, E. M. J., S. Singh and R. Kluger, Org. Biomol. Chem., 2015, 13, 10244-10249.

Snyder, S. R., Welty, E. V., Walder, R. Y., Williams, L. A., and Walder, J. A. (1987) HbXL99 alpha: a hemoglobin derivative that is cross-linked between the alpha subunits is useful as a blood substitute, Proceedings of the National Academy of Sciences 84, 7280-7284.

Vandegriff, K. D., Young, M. A., Keipert, P. E., and Winslow, R. M. (2007) The safety profile of Hemospan®: a new oxygen therapeutic designed using maleimide poly (ethylene) glycol conjugation to human hemoglobin, Transfusion Alternatives in Transfusion Medicine 9, 213-225.

Wang, Z.-X., Ravi Kumar, N., and Srivastava, D. K. (1992) A novel spectroscopic titration method for determining the dissociation constant and stoichiometry of protein-ligand complex, Analytical Biochemistry 206, 376-381.

Webster, K. D., D. Dahhan, C. Frosti, W. Dean, J. B. Chaires and K. W. Olsen, FASEB J., 2016, 30, 825.3.

Wendeln, C., I. Singh, S. Rinnen, C. Schulz, H. F. Arlinghaus, G. A. Burley and B. J. Ravoo, Chem. Sci., 2012, 3, 2479-2484.

Yang, H., P. Srivastava, C. Zhang and J. C. Lewis, ChemBioChem, 2014, 15, 223-227.

Yang, Y. and R. Kluger, Chem. Commun., 2010, 46, 7557-7559.

Yu, S., Yao, P., Jiang, M., and Zhang, G. (2006) Nanogels prepared by self-assembly of oppositely charged globular proteins, Biopolymers 83, 148-158.

Zeng, D., B. M. Zeglis, J. S. Lewis and C. J. Anderson, J. Nucl. Med., 2013, 54, 829-832.

What is claimed is:

1. A hemoglobin based oxygen carrier (HBOC) comprising a first hemoglobin protein cross-linked by a strain-promoted alkyne-azide cycloaddition (SPAAC) reaction or a strain-promoted alkyne-nitrone cycloaddition (SPANC) reaction, in absence of copper ions to a second hemoglobin protein, wherein said hemoglobin protein comprises two alpha and two beta subunits, said HBOC being capable of binding oxygen and releasing same in a similar manner as in whole blood.

2. The HBOC of claim 1, wherein said first hemoglobin protein comprises hemoglobin covalently linked to an angle strained cycloalkyne moiety and said second hemoglobin protein comprises hemoglobin, the beta subunits of which are covalently linked to an azide or nitrone moiety, wherein said cycloalkyne moiety and said azide or nitrone moiety react together according to said SPAAC or SPANC reaction covalently linking together in a copper-free reaction said first hemoglobin protein to said second hemoglobin protein.

3. The HBOC of claim 1 wherein said first hemoglobin protein and said second hemoglobin protein, each comprises hemoglobin covalently linked to an angle strained cycloalkyne moiety, said cycloalkyne moiety of said first and second hemoglobin proteins reacting with a compound comprising at least 2 azide moieties or nitrones moieties according to said SPAAC or SPANC reaction covalently linking together in a copper-free reaction said first hemoglobin protein to said second hemoglobin protein.

4. The HBOC of claim 2, wherein the angle strained cycloalkyne moiety is a $C_8$-$C_9$ cycloalkyne moiety.

5. The HBOC of claim 2, wherein the angle strained cycloalkyne moiety is a cyclooctyne moiety.

6. The HBOC of claim 1, wherein said hemoglobin is deoxyhemoglobin, carbonmonoxyhemoglobin or oxyhemoglobin.

7. The HBOC of claim 2, wherein the cycloalkyne moiety is attached via a chemical cross-link to the beta subunits of the hemoglobin.

8. The HBOC of claim 1, wherein the two beta subunits of each hemoglobin are cross-linked together.

9. The HBOC of claim 8, wherein amino groups of lysine residues of the beta subunits of each hemoglobin are cross-linked together.

10. The HBOC of claim 8, wherein the N-terminal residues of the beta subunits of each hemoglobin are cross-linked via their alpha amino groups to amino groups of lysine residues.

11. The HBOC of claim 9, wherein said lysine residues are located at a position corresponding to amino acid residue 82 or 144 of SEQ ID NO:1.

12. The HBOC of claim 1, wherein the two alpha subunits of each hemoglobin are cross-linked together.

13. The HBOC of claim 12, wherein the epsilon amino groups of lysine residues of the alpha subunits of each hemoglobin are cross-linked together.

14. The HBOC of claim 13, wherein said lysine residues are located at a position corresponding to amino acid residue 99 of SEQ ID NO:2.

15. A composition for use in a method for increasing oxygen transport, said composition comprising the hemoglobin based oxygen carrier (HBOC) as defined in claim 1 and a suitable excipient or carrier.

16. A composition for use in perfusion, said composition comprising the hemoglobin based oxygen carrier (HBOC) as defined in claim 1 and a suitable excipient or carrier.

17. The HBOC of claim 3, wherein the angle strained cycloalkyne moiety is a $C_8$-$C_9$ cycloalkyne moiety.

18. The RBOC of claim 3, wherein the angle strained cycloalkyne moiety is a cycloalkyne moiety.

* * * * *

SEQUENCE LISTING

<160> NUMBER OF SEQ ID NOS: 2

<210> SEQ ID NO 1
<211> LENGTH: 146
<212> TYPE: PRT
<213> ORGANISM: Homo sapiens

<400> SEQUENCE: 1

Val His Leu Thr Pro Glu Glu Lys Ser Ala Val Thr Ala Leu Trp Gly
1               5                   10                  15

Lys Val Asn Val Asp Glu Val Gly Gly Glu Ala Leu Gly Arg Leu Leu
            20                  25                  30

```
Val Val Tyr Pro Trp Thr Gln Arg Phe Phe Glu Ser Phe Gly Asp Leu
            35              40              45

Ser Thr Pro Asp Ala Val Met Gly Asn Pro Lys Val Lys Ala His Gly
        50              55              60

Lys Lys Val Leu Gly Ala Phe Ser Asp Gly Leu Ala His Leu Asp Asn
65              70              75                          80

Leu Lys Gly Thr Phe Ala Thr Leu Ser Glu Leu His Cys Asp Lys Leu
                85              90                      95

His Val Asp Pro Glu Asn Phe Arg Leu Leu Gly Asn Val Leu Val Cys
            100             105             110

Val Leu Ala His His Phe Gly Lys Glu Phe Thr Pro Pro Val Gln Ala
        115             120             125

Ala Tyr Gln Lys Val Val Ala Gly Val Ala Asn Ala Leu Ala His Lys
        130             135             140

Tyr His
145

<210> SEQ ID NO 2
<211> LENGTH: 141
<212> TYPE: PRT
<213> ORGANISM: Homo sapiens

<400> SEQUENCE: 2

Val Leu Ser Pro Ala Asp Lys Thr Asn Val Lys Ala Ala Trp Gly Lys
1               5                   10                  15

Val Gly Ala His Ala Gly Glu Tyr Gly Ala Glu Ala Leu Glu Arg Met
            20                  25                  30

Phe Leu Ser Phe Pro Thr Thr Lys Thr Tyr Phe Pro His Phe Asp Leu
        35                  40                  45

Ser His Gly Ser Ala Gln Val Lys Gly His Gly Lys Lys Val Ala Asp
    50                  55                  60

Ala Leu Thr Asn Ala Val Ala His Val Asp Asp Met Pro Asn Ala Leu
65                  70                  75                  80

Ser Ala Leu Ser Asp Leu His Ala His Lys Leu Arg Val Asp Pro Trp
                85                  90                  95

Asn Phe Lys Leu Leu Ser His Cys Leu Leu Val Thr Leu Ala Ala His
            100                 105                 110

Leu Pro Ala Glu Phe Thr Pro Ala Val His Ala Ser Leu Asp Lys Phe
        115                 120                 125

Leu Ala Ser Val Ser Thr Val Leu Thr Ser Lys Tyr Arg
        130                 135                 140
```